US012799139B2

(12) United States Patent
Haemori et al.

(10) Patent No.: US 12,799,139 B2
(45) Date of Patent: Nov. 17, 2026

(54) COMPOUND, COMPOSITION, ELECTROCONDUCTIVE AID, ELECTRODE, AND LAMINATE

(71) Applicants: IDEMITSU KOSAN CO., LTD., Tokyo (JP); THE UNIVERSITY OF TOKYO, Tokyo (JP)

(72) Inventors: Masamitsu Haemori, Tokyo (JP); Shigekazu Tomai, Tokyo (JP); Yoshikatsu Seino, Tokyo (JP); Hiroaki Nakamura, Tokyo (JP); Hatsumi Mori, Tokyo (JP); Tomoko Fujino, Tokyo (JP); Shun Dekura, Tokyo (JP); Kota Onozuka, Tokyo (JP)

(73) Assignees: IDEMITSU KOSAN CO., LTD., Tokyo (JP); THE UNIVERSITY OF TOKYO, Tokyo (JP)

( * ) Notice: Subject to any disclaimer, the term of this patent is extended or adjusted under 35 U.S.C. 154(b) by 126 days.

(21) Appl. No.: 18/686,985

(22) PCT Filed: Aug. 17, 2022

(86) PCT No.: PCT/JP2022/031091
§ 371 (c)(1),
(2) Date: Feb. 27, 2024

(87) PCT Pub. No.: WO2023/032676
PCT Pub. Date: Mar. 9, 2023

(65) Prior Publication Data

US 2024/0317778 A1 Sep. 26, 2024

(30) Foreign Application Priority Data

Aug. 30, 2021 (JP) ................................ 2021-140507

(51) Int. Cl.
*C07D 519/00* (2006.01)
*H01B 1/12* (2006.01)
(Continued)

(52) U.S. Cl.
CPC ........... *C07D 519/00* (2013.01); *H01B 1/127* (2013.01); *H01G 11/48* (2013.01); *H01M 4/624* (2013.01)

(58) Field of Classification Search
CPC ......... H01B 1/00; H01B 1/127; H01M 4/624; C07D 5/12
See application file for complete search history.

(56) References Cited

U.S. PATENT DOCUMENTS 8,114,955 B2 * 2/2012 Ying ...................... H01B 1/127 528/380
11,773,213 B2 * 10/2023 He ....................... C08G 61/126 528/42

(Continued)

FOREIGN PATENT DOCUMENTS

CN 107739430 A 2/2018
JP 2014-70066 A 4/2014

(Continued)

OTHER PUBLICATIONS

Pai et al "Electronic structure and properties of alternating donor-acceptor conjugated copolymers: 3,4-Ethylenedioxythiophene (EDOT) copolymers and model compounds", Polymer 47 (2006) 699-708.*

(Continued)

*Primary Examiner* — Mark Kopec
(74) *Attorney, Agent, or Firm* — Oblon, McClelland, Maier & Neustadt, L.L.P.

(57) ABSTRACT

A compound of formula (1):

$$Z^1\text{-}\alpha_a\text{-}\beta_b\text{-}\gamma_c\text{-}\delta_d\text{-}\varepsilon_e\text{-}Z^2 \quad (1),$$

wherein α, β, γ, δ, and ε are respectively units of formulas (1α), (1β), (1γ), (1δ), and (1ε):

(1α)

(1β)

(1γ)

(1δ)

and (Continued)

-continued (1ε)

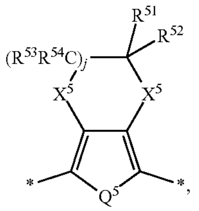

and the structure of the unit α is different from the structure of the unit β, the structure of the unit β is different from the structure of the unit γ, the structure of the unit γ is different from the structure of the unit δ, and the structure of the unit δ is different from the structure of the unit ε.

24 Claims, 1 Drawing Sheet

(51) Int. Cl.
*H01G 11/48* (2013.01)
*H01M 4/62* (2006.01)

(56) References Cited

U.S. PATENT DOCUMENTS

2014/0370297 A1* 12/2014 Kim ....................... H01B 1/127
252/500
2017/0062090 A1* 3/2017 Alsayed ................... H01B 1/02

FOREIGN PATENT DOCUMENTS

KR 20160005250 A * 1/2016
WO WO-2011075644 A2 * 6/2011 ............. C08G 61/12
WO WO 2020/262443 A1 12/2020

OTHER PUBLICATIONS

Chen et al "Preparation and Characterization of Aqueous Dispersions of Poly(3,4-ethylenedithiathiophene-co-3,4-ethylenedioxythiophene)/ Poly(styrene sulfonate) and Their Conducting Films", J. Appl. Polym. Sci. 2013, DOI: 10.1002/APP.38571.*

International Preliminary Report on Patentability and Written Opinion issued Mar. 5, 2024 in PCT/JP2022/031091, 6 pages.

International Search Report issued Nov. 1, 2022 in PCT/JP2022/031091, 2 pages.

Nishinaga, et al., "Stable Radical Cations and their π-Dimers prepared from Ethylene-and Propylene-3, 4-dioxythiophene Co-oligomers: Combined Experimental and Theoretical Investigations", The journal of Organic Chemistry, 2017, vol. 82, pp. 7245-7253.

Lin et al., "Structural, Optical, and Electronic Properties of a Series of 3,4-Propylenedioxythiophene Oligomers in Neutral and Various Oxidation States", Journal of the American Chemical Society, 2011, vol. 133, pp. 11339-11350.

Toufik et al., "The Opto-Electronic Properties and Molecular Design of New Materials Based on Pyrrole, DFT Study", Journal of Physical Studies, 2012, col. 16, pp. 1702-1-1702-8.

Spencer et al., "The first direct experimental comparison between the hugely contrasting properties of PEDOT and the all-sulfur analogue PEDTT by analogy with well-defined EDTT-EDOT copolymers," Journal of Materials Chemistry, vol. 15, 2005, pp. 4783-4792.

Poater et al., "Examining the planarity of poly(3,4-ethylenedioxythiophene): consideration of self-rigidification, electronic, and geometric effects" The Journal of Physical Chemistry A, vol. 114, 2009, 6 pages.

Japanese Office Action issued Mar. 11, 2025 in Japanese Patent Application No. 2021-140507 (with unedited computer-generated English translation), 8 pages.

* cited by examiner (a)
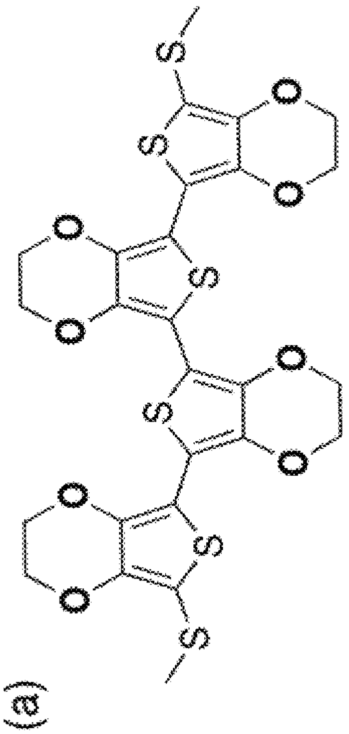
(b)
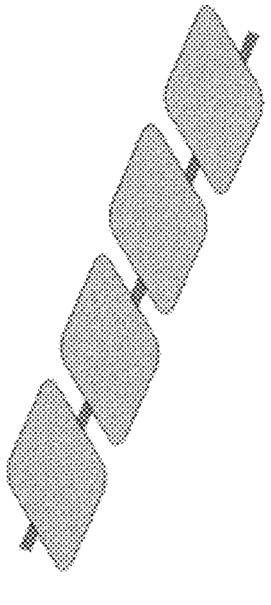
(c)
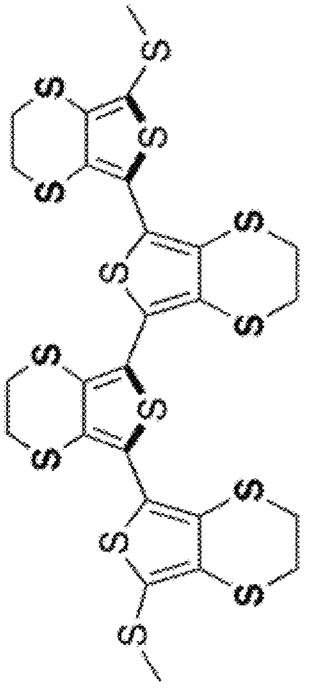
(d)
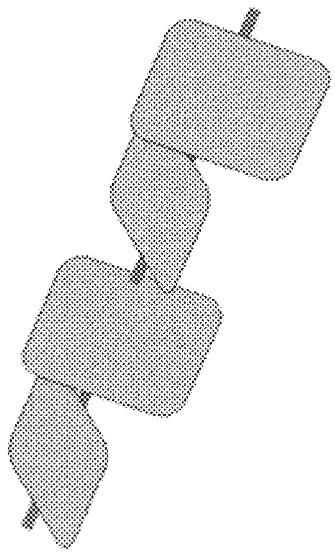
(PRIOR ART)

COMPOUND, COMPOSITION, ELECTROCONDUCTIVE AID, ELECTRODE, AND LAMINATE

CROSS-REFERENCE TO RELATED APPLICATIONS

The present application is the national stage of international application PCT/JP2022/031091, filed on Aug. 17, 2022, and claims the benefit of the filing date of Japanese Appl. No. 2021-140507, filed on Aug. 30, 2021.

TECHNICAL FIELD

The invention relates to a compound, a composition, a conductive aid, an electrode, and a laminated body.

Specifically, the invention relates to a compound, a composition, a conductive aid, an electrode, and a laminated body having excellent conductivity.

BACKGROUND ART

Patent Document 1 discloses a conductive oligomer having a specific molecular structure.

RELATED ART DOCUMENTS

Patent Documents

[Patent Document 1] WO 2020262443 A1

SUMMARY OF THE INVENTION

However, in the prior arts, including Patent Document 1, further room for improvement in terms of conductivity was found.

An object of the invention is to provide a compound, a composition, a conductive aid, an electrode, and a laminated body having excellent conductivity.

As a result of intensive studies, the inventors have found that a compound having a specific structure in which a plurality of types of units is continuously concatenated has excellent conductivity, and have completed the invention.

According to the invention, the following compound and so on can be provided.

A compound represented by the following formula (1):

$$Z^1\text{-}\alpha_a\text{-}\beta_b\text{-}\gamma_c\text{-}\delta_d\text{-}\varepsilon_e\text{-}Z^2 \quad (1)$$

wherein in the formula (1),

α is a unit represented by the following formula (1α), and a is an integer of 1 to 10; when a is two or more, two or more units α are the same as each other;

β is a unit represented by the following formula (1β), and b is an integer of 1 to 10; when b is two or more, two or more units β are the same as each other;

γ is a unit represented by the following formula (1γ), and c is an integer of 1 to 10; when c is two or more, two or more units γ are the same as each other;

δ is a unit represented by the following formula (1δ), and d is an integer of 0 to 10; when d is two or more, two or more units δ are the same as each other;

ε is a unit represented by the following formula (1ε), and e is an integer of 0 to 10; when e is two or more, two or more units ε are the same as each other;

the structure of unit α is different from the structure of unit β;

the structure of unit β is different from the structure of unit γ;

the structure of unit γ is different from the structure of unit δ;

the structure of unit δ is different from the structure of unit ε;

$Z^1$ and $Z^2$ are independently $Y^1$, $Y^2R^1$, or $CR^2R^3R^4$;

$Y^1$ is H (hydrogen atom), F (fluorine atom), Cl (chlorine atom), Br (bromine atom), I (iodine atom), or a substituted or unsubstituted aryl group including 6 to 22 ring carbon atoms, and when two $Y^1$'s are present, the two $Y^1$'s are the same as or different from each other;

$Y^2$ is S (sulfur atoms), Se (selenium atom), O (oxygen atom), Te (tellurium atom), $SO_3$ (S is a sulfur atom, O is an oxygen atom), $SO_2$ (S is a sulfur atom, O is an oxygen atom), or $PO_3$ (P is a phosphorus atom, O is an oxygen atom), and when two $Y^2$'s are present, the two $Y^2$'s are the same as or different from each other;

$R^1$ to $R^4$ are independently H (hydrogen atom), a substituted or unsubstituted alkyl group including 1 to 12 carbon atoms, or a substituted or unsubstituted aryl group including 6 to 22 ring carbon atoms;

when two $R^1$'s are present, the two $R^1$'s are the same as or different from each other;

when two $R^2$'s are present, the two $R^2$'s are the same as or different from each other;

when two $R^3$'s are present, the two $R^3$'s are the same as or different from each other;

when two $R^4$'s are present, the two $R^4$'s are the same as or different from each other;

(1α)

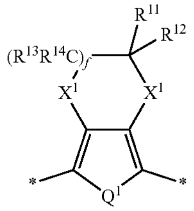

wherein in the formula (1α), $Q^1$ is S (sulfur atom), Se (selenium atom), O (oxygen atom), Te (tellurium atom), or NH;

$X^1$ is S (sulfur atom), Se (selenium atom), O (oxygen atom), or Te (tellurium atom), and two $X^1$'s are the same as each other;

$R^{11}$ to $R^{14}$ are independently H (hydrogen atom) or an unsubstituted alkyl group including 1 to 12 carbon atoms;

f is an integer of 1 to 3;

when f is two or more, two or more $R^{13}$'s are the same as or different from each other, and two or more $R^{14}$'s are the same as or different from each other;

(1β)

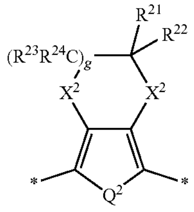

wherein in the formula (1β), $Q^2$ is S (sulfur atom), Se (selenium atom), O (oxygen atom), Te (tellurium atom), or NH;

$X^2$ is S (sulfur atom), Se (selenium atom), O (oxygen atom), or Te (tellurium atom), and two $X^2$'s are the same as each other;

$R^{21}$ to $R^{24}$ are independently H (hydrogen atom) or an unsubstituted alkyl group including 1 to 12 carbon atoms;

g is an integer of 1 to 3;

when g is two or more, two or more $R^{23}$'s are the same as or different from each other, and two or more $R^{24}$'s are the same as or different from each other;

(1γ)

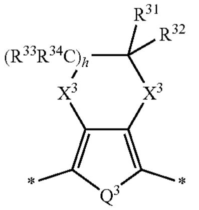

wherein in the formula (1γ), $Q^3$ is S (sulfur atom), Se (selenium atom), O (oxygen atom), Te (tellurium atom), or NH;

$X^3$ is S (sulfur atom), Se (selenium atom), O (oxygen atom), or Te (tellurium atom), and two $X^3$'s are the same as each other;

$R^{31}$ to $R^{34}$ are independently H (hydrogen atom) or an unsubstituted alkyl group including 1 to 12 carbon atoms;

h is an integer of 1 to 3;

when h is two or more, two or more $R^{33}$'s are the same as or different from each other, and two or more $R^{34}$'s are the same as or different from each other;

(1δ)

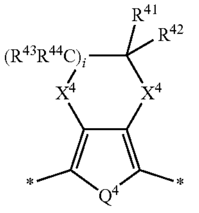

wherein in the formula (1δ), $Q^4$ is S (sulfur atom), Se (selenium atom), O (oxygen atom), Te (tellurium atom), or NH;

$X^4$ is S (sulfur atom), Se (selenium atom), O (oxygen atom), or Te (tellurium atom), and two $X^4$'s are the same as each other;

$R^{41}$ to $R^{44}$ are independently H (hydrogen atom) or an unsubstituted alkyl group including 1 to 12 carbon atoms;

i is an integer of 1 to 3;

when i is two or more, two or more $R^{43}$'s are the same as or different from each other, and two or more $R^{44}$'s are the same as or different from each other;

(1ε)

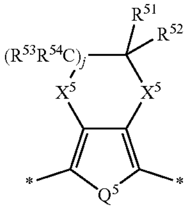

wherein in the formula (1ε), $Q^5$ is S (sulfur atom), Se (selenium atom), O (oxygen atom), Te (tellurium atom), or NH;

$X^5$ is S (sulfur atom), Se (selenium atom), O (oxygen atom), or Te (tellurium atom), and two $X^5$'s are the same as each other;

$R^{51}$ to $R^{54}$ are independently H (hydrogen atom) or an unsubstituted alkyl group including 1 to 12 carbon atoms;

j is an integer of 1 to 3;

when j is two or more, two or more $R^{53}$'s are the same as or different from each other, and two or more $R^{54}$'s are the same as or different from each other.

According to the invention, it is possible to provide a compound, a composition, a conductive aid, an electrode, and a laminated body having excellent conductivity.

BRIEF DESCRIPTION OF THE DRAWINGS

FIG. 1(*a*) to (*d*) show a conceptual illustration of planarization inhibition and crystallization inhibition in a conventional conductive oligomer (comparison), with FIGS. 1(*a*) and (*b*) showing an oligomer of the same unit having oxygen bonded to an aromatic ring exhibiting conjugate extension that decreases stability to oxidation and decreases solubility, and FIGS. 1(*c*) and (*d*) showing an oligomer of the same unit having sulfur bonded to an aromatic ring having increased stability to oxidation and solubility due to its twisted structure.

MODE FOR CARRYING OUT THE INVENTION

Hereinafter, the compound, the composition, the conductive aid, the electrode, and the laminated body of the invention will be described in detail.

In this specification, "x to y" represents a numerical value range of "x or more and y or less." The upper and lower limits stated for the numerical value ranges can be combined arbitrarily. Any combinations of two or more of the embodiments described below are also embodiments of the invention.

In this specification, to a bondable position at which a symbol such as "R", or "Y" representing a deuterium atom is not specified in a chemical formula, a hydrogen atom, that is, a protium atom, a deuterium atom, or a tritium atom is bonded.

In this specification, the number of ring carbon atoms represents only the number of carbon atoms forming the ring among carbon atoms of a compound having a structure in which atoms are bonded in a ring form (for example, a monocyclic compound, a fused ring compound, a cross-linked compound, a carbocyclic compound, or a heterocyclic compound). When the ring is substituted by a substituent, carbon atoms contained in the substituent are not included in the number of ring carbon atoms. The same shall apply to "the number of ring carbon atoms" described below, unless otherwise specified. For example, a benzene ring includes 6 ring carbon atoms and a naphthalene ring includes 10 ring carbon atoms.

In this specification, "XX to YY carbon atoms" in the expression "a substituted or unsubstituted ZZ group including XX to YY carbon atoms" represents the number of carbon atoms in the case where the ZZ group is unsubstituted by a substituent, and does not include the number of carbon atoms of a substituent in the case where the ZZ group is substituted by the substituent. The number of carbon atoms is selected as an integer. The same applies to the case where the number of carbon atoms is the number of ring carbon atoms.

The "substituted ZZ group" means a group in which one or more hydrogen atoms of the "unsubstituted ZZ group" are substituted with a substituent.

The "unsubstituted ZZ group" means that hydrogen atoms in the ZZ group are not substituted with a substituent. Hydrogen atoms of the "unsubstituted ZZ group" are a protium atom, a deuterium atom, or a tritium atom.

1. Compound

The compound according to an aspect of the invention is represented by the following formula (1):

$$Z^1\text{-}\alpha_a\text{-}\beta_b\text{-}\gamma_c\text{-}\delta_d\text{-}\varepsilon_e\text{-}Z^2 \quad (1)$$

wherein in the formula (1),

α is a unit represented by the following formula (1α), and a is an integer of 1 to 10; when a is two or more, two or more units α are the same as each other;

β is a unit represented by the following formula (1β), and b is an integer of 1 to 10; when b is two or more, two or more units 1 are the same as each other;

γ is a unit represented by the following formula (1γ), and c is an integer of 1 to 10; when c is two or more, two or more units γ are the same as each other;

δ is a unit represented by the following formula (1δ), and d is an integer of 0 to 10; when d is two or more, two or more units δ are the same as each other;

ε is a unit represented by the following formula (1ε), and e is an integer of 0 to 10; when e is two or more, two or more units ε are the same as each other;

the structure of unit α is different from the structure of unit β;

the structure of unit β is different from the structure of unit γ;

the structure of unit γ is different from the structure of unit δ;

the structure of unit δ is different from the structure of unit ε;

$Z^1$ and $Z^2$ are independently $Y^1$, $Y^2R^1$, or $CR^2R^3R^4$;

$Y^1$ is H (hydrogen atom), F (fluorine atom), Cl (chlorine atom), Br (bromine atom), I (iodine atom), or a substituted or unsubstituted aryl group including 6 to 22 ring carbon atoms, and when two $Y^1$'s are present, the two $Y^1$'s are the same as or different from each other;

$Y^2$ is S (sulfur atoms), Se (selenium atom), O (oxygen atom), Te (tellurium atom), $SO_3$ (S is a sulfur atom, O is an oxygen atom), $SO_2$ (S is a sulfur atom, O is an oxygen atom), or $PO_3$ (P is a phosphorus atom, O is an oxygen atom), and when two $Y^2$'s are present, the two $Y^2$'s are the same as or different from each other;

$R^1$ to $R^4$ are independently H (hydrogen atom), a substituted or unsubstituted alkyl group including 1 to 12 carbon atoms, or a substituted or unsubstituted aryl group including 6 to 22 ring carbon atoms;

when two $R^1$'s are present, the two $R^1$'s are the same as or different from each other, when two $R^2$'s are present, the two $R^2$'s are the same as or different from each other;

when two $R^3$'s are present, the two $R^3$'s are the same as or different from each other;

when two $R^4$'s are present, the two $R^4$'s are the same as or different from each other;

(1α)

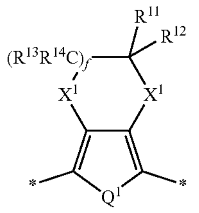

wherein in the formula (1α), $Q^1$ is S (sulfur atom), Se (selenium atom), O (oxygen atom), Te (tellurium atom), or NH;

$X^1$ is S (sulfur atom), Se (selenium atom), O (oxygen atom), or Te (tellurium atom), and two $X^1$'s are the same as each other;

$R^{11}$ to $R^{14}$ are independently H (hydrogen atom) or an unsubstituted alkyl group including 1 to 12 carbon atoms;

f is an integer of 1 to 3;

when f is two or more, two or more $R^{13}$'s are the same as or different from each other, and two or more $R^{14}$'s are the same as or different from each other;

(1β)

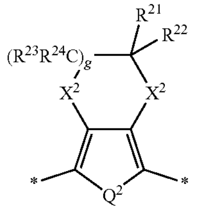

wherein in the formula (1β), $Q^2$ is S (sulfur atom), Se (selenium atom), O (oxygen atom), Te (tellurium atom), or NH;

$X^2$ is S (sulfur atom), Se (selenium atom), O (oxygen atom), or Te (tellurium atom), and two $X^2$'s are the same as each other;

$R^{21}$ to $R^{24}$ are independently H (hydrogen atom) or an unsubstituted alkyl group including 1 to 12 carbon atoms;

g is an integer of 1 to 3;

when g is two or more, two or more $R^{23}$'s are the same as or different from each other, and two or more $R^{24}$'s are the same as or different from each other;

(1γ)

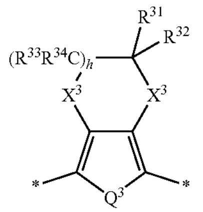

wherein in the formula (1γ), $Q^3$ is S (sulfur atom), Se (selenium atom), O (oxygen atom), Te (tellurium atom), or NH;

$X^3$ is S (sulfur atom), Se (selenium atom), O (oxygen atom), or Te (tellurium atom), and two X's are the same as each other;

$R^{31}$ to $R^{34}$ are independently H (hydrogen atom) or an unsubstituted alkyl group including 1 to 12 carbon atoms;

h is an integer of 1 to 3;

when h is two or more, two or more $R^{33}$'s are the same as or different from each other, and two or more $R^{34}$'s are the same as or different from each other;

(1δ)

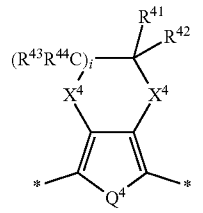

wherein in the formula (1δ), $Q^4$ is S (sulfur atom), Se (selenium atom), O (oxygen atom), Te (tellurium atom), or NH;

$X^4$ is S (sulfur atom), Se (selenium atom), O (oxygen atom), or Te (tellurium atom), and two $X^4$'s are the same as each other;

$R^{41}$ to $R^{44}$ are independently H (hydrogen atom) or an unsubstituted alky group including 1 to 12 carbon atoms;

i is an integer of 1 to 3;

when i is two or more, two or more $R^{43}$'s are the same as or different from each other, and two or more $R^{44}$'s are the same as or different from each other;

(1ε)

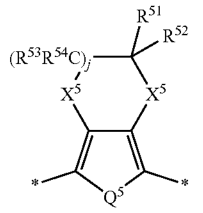

wherein in the formula (1ε), $Q^5$ is S (sulfur atom), Se (selenium atom), O (oxygen atom), Te (tellurium atom), or NH;

$X^5$ is S (sulfur atom), Se (selenium atom), O (oxygen atom), or Te (tellurium atom), and two $X^5$'s are the same as each other;

$R^{51}$ to $R^{54}$ are independently H (hydrogen atom) or an unsubstituted alkyl group including 1 to 12 carbon atoms;

j is an integer of 1 to 3;

when j is two or more, two or more $R^{53}$'s are the same as or different from each other, and two or more $R^{54}$'s are the same as or different from each other.

The compound according to this aspect is excellent in conductivity. The reason for obtaining such an effect is not necessarily clear and is estimated as follows:

First, considering the electronic state of the conductive oligomer disclosed in Patent Document 1, it is suggested that the inter-electron Coulomb repulsion is in a semi-filled Mott insulating state that exceeds the bandwidth. This suggests that the reduction of Coulomb repulsion by the conjugate length expansion accompanied with chain elongation is effective in achieving further high conductivity. FIG. 1 is a conceptual illustration of planarization inhibition and crystallization inhibition when oxygen or sulfur is bonded to an aromatic ring in a conventional conductive oligomer (comparative) as an example. As shown in FIG. 1 (*a*) and (*b*), an oligomer formed by linking only the same unit having oxygen bonded to an aromatic ring is difficult to synthesize and isolate because an increase in the highest occupied level due to the conjugate extension increases the instability to oxidation and further decreases the solubility. On the other hand, an oligomer formed by linking only the same unit having sulfur bonded to an aromatic ring as shown in FIGS. 1(*c*) and (*d*) is increased in the stability against oxidation and solubility by its twisted structure. However, the longer the chain becomes, the more the molecular planarization after addition of a dopant is prevented. Therefore, after when a dopant is added (in other words, after oxidation), the effect of reducing the Coulomb repulsion is weakened, and crystallization is also prevented. Further, such an oligomer formed by linking the same units tends to form voids in the crystal as the chain becomes longer, which makes the single crystallization difficult. Due to results of these factors, there is a limit to increase in conductivity.

On the other hand, since the compound according to this aspect is formed by linking a plurality of specific types of units, the inhibitory effect against the conductivity exhibition in stated for the above-described prior art is greatly reduced. Therefore, the activation-energy $E_a$ becomes lower, and excellent conductivity is exhibited.

According to the compound of this aspect, it is also possible to finely adjust the degrees of planarization, solubility, and suppression of voids after oxidation. Specifically, a block composed of units having a solubility auxiliary group, a block having a twisted structure due to steric repulsion caused by continuing the units (the block can increase solubility, and structural stability in a neutral state), a block for sterically filling voids (for example, a block composed of sterically larger units than other blocks, such as a unit having a moderately bulky substituent, a unit having a large number of constituent atoms, etc.), and the like are arranged as appropriate, so that it is possible to fill voids in the crystal while ensuring high solubility and stability against oxidation. As a result, it is possible to sufficiently reduce the inter-electron Coulomb repulsion due to the conjugate extension by elongation of the chain. Dimensionality can also be obtained. In addition, effective intermolecular orbital interactions can be obtained. In this way, the activation-energy $E_a$ can be further reduced, and more excellent conductivity can be exhibited.

In one embodiment, the difference between the structure of the unit α and the structure of the unit β is one or more differences selected from the group consisting of the difference in $Q^1$ and $Q^2$, the difference in $X^1$ and $X^2$, the difference in $R^{11}$ and $R^{21}$, the difference in $R^{12}$ and $R^{22}$, the difference in $R^{13}$ and $R^{23}$, the difference in $R^{14}$ and $R^{24}$, and the difference in f and g. When f and g are different from each other, f and g may be f>g or f<g.

In one embodiment, the difference between the structure of the unit β and the structure of the unit γ is one or more differences selected from the group consisting of the difference in $Q^2$ and $Q^3$, the difference in $X^2$ and $X^3$, the difference in $R^{21}$ and $R^{31}$, the difference in $R^{22}$ and $R^{32}$, the difference in $R^{23}$ and $R^{33}$, the difference in $R^{24}$ and $R^{34}$, and the difference in g and h. When g and h are different from each other, g and h may be g>h or g<h.

In one embodiment, the difference between the structure of the unit γ and the structure of the unit δ is one or more differences selected from the group consisting of the difference in $Q^3$ and $Q^4$, the difference in $X^3$ and $X^4$, the difference in $R^{31}$ and $R^{41}$, the difference in $R^{32}$ and $R^{42}$, the difference in $R^{33}$ and $R^{43}$, the difference in $R^{34}$ and $R^{44}$, and the difference in h and i. When h and i are different from each other, h and i may be h>i or h<i.

In one embodiment, the difference between the structure of the unit δ and the structure of the unit ε is one or more differences selected from the group consisting of the difference in $Q^4$ and $Q^5$, the difference in $X^4$ and $X^5$, the difference in $R^{41}$ and $R^{51}$, the difference in $R^{42}$ and $R^{52}$, the difference in $R^{43}$ and $R^{53}$, the difference in $R^{44}$ and $R^{54}$, and the difference in i and j. When i and j are different from each other, i and j may be i>j or i<j.

In one embodiment, $Q^1$ is S (sulfur atom). This further increases the conductivity.

In one embodiment, $X^1$ is S (sulfur atom) or O (oxygen atom). This further increases the conductivity.

In one embodiment, the number of carbon atoms of the alkyl group for $R^{11}$ to $R^{14}$ are independently 1 to 12, 1 to 11, 1 to 10, 1 to 9, 1 to 8, 1 to 7, 1 to 6, 1 to 5, 1 to 4, 1 to 3, or 1 to 2. In one embodiment, the number of carbon atoms of the alkyl group for $R^{11}$ to $R^{14}$ are independently 1, 2, 3, 4, 5, 6, 7, 8, 9, 10, 11, or 12. The less the number of carbon atoms of the alkyl group for $R^{11}$ to $R^{14}$ is, the higher the conductivity increases.

In one embodiment, when the number of carbon atoms is 3 or more, the alkyl group for $R^{11}$ to $R^{14}$ are independently linear or branched. By the alkyl group for $R^{11}$ to $R^{14}$ being linear, the conductivity of the compound further increases. By the alkyl group for $R^{11}$ to $R^{14}$ being branched, solubility of the compound in various solvents increases.

In one embodiment, f is an integer of 1 to 3, an integer of 1 to 2, or 1. When f is 1 or 2, the conductivity is further increased.

In one embodiment, the unit α is represented by the following formula (2):

(2)

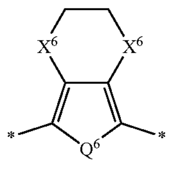

wherein in the formula (2), $Q^6$ is S (sulfur atom), Se (selenium atom), O (oxygen atom), Te (tellurium atom), or NH; and $X^6$ is S (sulfur atom), Se (selenium atom), O (oxygen atom), or Te (tellurium atom), and two $X^6$'s are the same as each other.

In one embodiment, $Q^6$ is S (sulfur atom).

In one embodiment, $X^6$ is S (sulfur atom) or O (oxygen atom).

In one embodiment, the unit α is represented by the following formula (3):

(3)

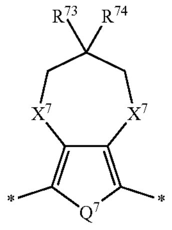

wherein in the formula (3), $Q^7$ is S (sulfur atom), Se (selenium atom), O (oxygen atom), Te (tellurium atom), or NH;

$X^7$ is S (sulfur atom), Se (selenium atom), O (oxygen atom), or Te (tellurium atom), and two $X^7$'s are the same as each other;

$R^{73}$ and $R^{74}$ are independently H (hydrogen atom) or an unsubstituted alkyl group including 1 to 12 carbon atoms.

In one embodiment, $Q^7$ is S (sulfur atom).

In one embodiment, $X^7$ is S (sulfur atom) or O (oxygen atom).

In one embodiment, $R^{73}$ and $R^{74}$ are independently an alkyl group including 1 to 12 carbon atoms.

In one embodiment, the unit α is represented by any one of the following formulas (U1) to (U3):

(U1)

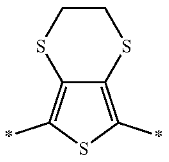

(U2)

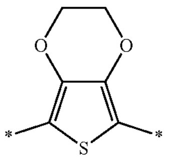

(U3)

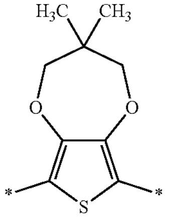

In one embodiment, a that represents the number of the unit α is an integer of 1 to 10, an integer of 1 to 9, an integer of 1 to 8, an integer of 1 to 7, an integer of 1 to 6, an integer of 1 to 5, an integer of 1 to 4, an integer of 1 to 3, an integer of 1 to 2, or 1. a that representing the number of the unit α is preferably an integer of 1 to 6, and more preferably an integer of 1 to 4. This further increases the conductivity.

For $Q^2$, $X^2$, $R^{21}$ to $R^{24}$, g, and b in the unit β, the explanations given for $Q^1$, $X^1$, $R^{11}$ to $R^{14}$, f, and a in the unit α are referred to, respectively.

In one embodiment, the unit β is represented by any one of the formulas (2), (3), and (U1) to (U3) given for the unit α.

For $Q^3$, $X^3$, $R^{31}$ to $R^{34}$, h, and c in the unit γ, the explanations given for $Q^1$, $X^1$, $R^{11}$ to $R^{14}$, f, and a in the unit α are referred to, respectively.

In one embodiment the unit γ is represented by any one of formulas (2), (3), and (U1) to (U3) given for the unit α.

For $Q^4$, $X^4$, $R^{41}$ to $R^{44}$, i, and d in the unit δ, the explanations given for $Q^1$, $X^1$, $R^{11}$ to $R^{14}$, f, and a in the unit α are referred to, respectively.

In one embodiment, the unit δ is represented by any one of the formulas (2), (3), and (U1) to (U3) given for the unit α.

For $Q^5$, $X^5$, $R^{51}$ to $R^{54}$, j, and e in the unit ε, the explanations given for $Q^1$, $X^1$, $R^{11}$ to $R^{14}$, f, and a in the unit α are referred to, respectively.

In one embodiment, the unit ε is represented by any one of the formulas (2), (3), and (U1) to (U3) given for the unit α.

In one embodiment, the structures of two or more units selected from the group consisting of the unit α, the unit β, the unit γ, the unit δ, and the unit ε are the same as each other.

In one embodiment, a and bare the same as or different from each other. That is, the relationship of a and b may be a=b, a>b, or a<b.

In one embodiment, band c are the same as or different from each other. That is, the relationship of b and c may be b=c, b>, or b<c.

In one embodiment, c and dare the same as or different from each other. That is, the relationship of c and d may be c=d, c>d, or c<d.

In one embodiment, d and e are the same as or different from each other. That is, the relationship of d and e may be d=e, d>e, or d<e.

In one embodiment, two or more selected from the group consisting of a, b, c, d, and e are the same value. Also, in one embodiment, two, three, four, or five selected from the group consisting of a, b, c, d, and e are the same value.

In one embodiment, one or more selected from the group consisting of a, b, c, d, and e are an integer of 1 to 6. Also, in one embodiment, one, two, three, four, or five selected from the group consisting of a, b, c, d, and e are an integer of 1 to 6.

In one embodiment, one or more selected from the group consisting of a, b, c, d, and e are an integer of 1 to 4. Also, in one embodiment, one, two, three, four, or five selected from the group consisting of a, b, c, d, and e are an integer of 1 to 4.

In one embodiment, one or more selected from the group consisting of f, g, h, i, and j are 1 or 2. Also, in one embodiment, one, two, three, four, or five selected from the group consisting of f, g, h, i, and j are 1 or 2.

In one embodiment, one or more selected from the group consisting of f, g, h, i, and j are 1. Also, in one embodiment, one, two, three, four, or five selected from the group consisting of f, g, h, i, and j are 1.

In one embodiment, one or more selected from the group consisting of $X^1$ to $X^5$ are the same as each other. Also, in one embodiment, one, two, three, four, or five selected from the group consisting of $X^1$ to $X^5$ are the same as each other.

In one embodiment, one or more selected from the group consisting of $X^1$ to $X^5$ are S (sulfur atom) or O (oxygen atom). Also, in one embodiment, one, two, three, four, or five selected from the group consisting of $X^1$ to $X^5$ are S (sulfur atom) or O (oxygen atom).

In one embodiment, one or more selected from the group consisting of $Q^1$ to $Q^5$ are the same as each other. Also, in one embodiment, one, two, three, four, or five selected from the group consisting of $Q^1$ to $Q^5$ are the same as each other.

In one embodiment, one or more selected from the group consisting of $Q^1$ to $Q^5$ are S (sulfur atom). Also, in one embodiment, one, two, three, four, or five selected from the group consisting of $Q^1$ to $Q^5$ are S (sulfur atom).

In one embodiment, one or more units selected from the group consisting of the unit α, the unit β, the unit γ, the unit δ, and the unit ε are represented by the formula (2). In one embodiment, one, two, three, four, or five units selected from the group consisting of the unit α, the unit β, the unit γ, the unit δ, and the unit ε are represented by the formula (2).

When two or more units selected from the group consisting of unit α, unit β, unit γ, unit δ, and unit ε are represented by the formula (2), the structures of the two or more units represented by the formula (2) are the same as or different from each other.

In one embodiment, one or more and four or less units selected from the group consisting of the unit α, the unit β, the unit γ, the unit δ, and the unit ε are represented by the formula (2), and among the unit α, the unit β, the unit γ, the unit δ, and the unit ε, units not represented by the formula (2) are represented by the formula (3).

In one embodiment, one or more units selected from the group consisting of the unit α, the unit β, the unit γ, the unit δ, and the unit ε are represented by the formula (3). In one embodiment, one, two, three, four, or five units selected from the group consisting of the unit α, the unit β, the unit γ, the unit δ, and the unit ε are represented by the formula (3).

When two or more units selected from the group consisting of the unit α, the unit β, the unit γ, the unit δ, and the unit ε are represented by the formula (3), the structures of the two or more units represented by the formula (3) are the same as or different from each other.

In one embodiment, one or more and four or less units selected from the group consisting of the unit α, the unit β, the unit γ, the unit δ, and the unit ε are represented by the formula (3), and among the unit α, the unit β, the unit γ, the unit δ, and the unit ε, units not represented by the formula (3) are represented by the formula (2).

In the above explanation, the unit represented by the formula (2) may be a unit represented by the formula (U1) or the formula (U2), and the unit represented by the formula (3) may be a unit represented by the formula (U3).

In one embodiment, d=0 and e=0 (hereinafter also referred to as "three-block form"). In this case, the compound contains three blocks in total in which a block composed of the unit α where the number thereof is a, a block composed of the unit β where the number thereof is b, and a block composed of the unit γ where the number thereof is c. Such a compound is represented by the following formula (13).

$$Z^1\text{-}\alpha_a\text{-}\beta_b\text{-}\gamma_c\text{-}Z^2 \qquad (1\text{-}3)$$

wherein in the formula (1-3), unit α, unit β, unit γ, a, b, c, $Z^1$, and $Z^2$ are as defined in the formula (1).

In one embodiment of the three-block form, the structure of the unit α and the structure of the unit γ are the same as each other.

In one embodiment of the three-block form, a and c are the same as each other (a=c).

In one embodiment, d is 1 or more and e=0 (hereinafter also referred to as "four-block form"). In this case, the compound contains four blocks in total in which a block composed of the unit α where the number thereof is a, a block composed of the unit β where the number thereof is b, a block composed of the unit γ where the number thereof is c, and a block composed of the unit δ where the number thereof is d. Such a compound is represented by the following formula (1-4).

$$Z^1\text{-}\alpha_a\text{-}\beta_b\text{-}\gamma_c\text{-}\delta_d\text{-}Z^2 \quad (1\text{-}4)$$

wherein in the formula (1-4), unit α, unit β, unit γ, unit δ, a, b, c, d, $Z^1$, and $Z^2$ are defined in the formula (1), provided that d is one or more.

In an embodiment of the four-block form, the structure of the unit α and the structure of the unit γ are the same as each other.

In an embodiment of the four-block form, the structure of the unit α and the structure of the unit δ are the same as each other.

In one embodiment of the four-block form, a and c are the same as each other (a=c).

In one embodiment of the four-block form, a and d are the same as each other (a=d).

In one embodiment, d is 1 or more and e is 1 or more (hereinafter, also referred to as "five-block form"). In this case, the compound contains five blocks in total in which a block composed of the unit α where the number thereof is a, a block of the unit β where the number thereof is b, a block composed of the unit γ where the number thereof is c, a block composed of the unit δ where the number thereof is d, and a block composed of the unit ε where the number thereof is e. Such a compound is represented by the following formula (1-5).

$$Z^1\text{-}\alpha_a\text{-}\beta_b\gamma_c\text{-}\delta_d\text{-}\varepsilon_e\text{-}Z^2 \quad (1\text{-}5)$$

wherein in the formula (1-5), unit α, unit β, unit γ, unit δ, unit ε, a, b, c, d, e, $Z^1$, and $Z^2$ are defined in the formula (1), provided that d is one or more and e is one or more.

In one embodiment of the five-block form, the structure of unit α and the structure of unit ε are the same as each other.

In one embodiment of the five-block form, the structure of unit β and the structure of unit δ are the same as each other.

In one embodiment of the five-block form, a and e are the same as each other (a=e).

In one embodiment of the five-block form, b and d are the same as each other (b=d).

In one embodiment, the number of ring carbon atoms of the aryl group for $Y^1$ is 6 to 22 or 6 to 14. The smaller the number of ring carbon atoms of the aryl group for $Y^1$ is, the more the solubility, conductivity, and heat resistance increase. In particular, the aryl group is preferably a phenyl group.

In one embodiment, when the aryl group for $Y^1$ is a substituted aryl group, specific examples of the substituent include a halogen group (halogen atom), $SR^6$ (S is a sulfur atom), $SeR^6$ (Se is a selenium atom), $OR^6$ (O is an oxygen atom), $SO_2R^6$ (S is a sulfur atom, and O is an oxygen atom), $PO_3R^6$ (P is a phosphorus atom, and O is an oxygen atom), an alkyl group including 1 to 12 carbon atoms, and the like. Specific examples of the halogen group include F (fluorine atom), Cl (chlorine atom), Br (bromine atom), and I (iodine atom). $R^6$ is H (hydrogen atom), an alkyl group including 1 to 12 carbon atoms, or an aryl group including 6 to 22 ring carbon atoms. In particular, the substituted aryl group is preferably an aryl group substituted with an alkyl group including 1 to 12 carbon atoms, and is preferably a p-tolyl group or an o-tolyl group, for example.

In one embodiment, the number of carbon atoms of the alkyl group for $R^1$ to $R^4$ are independently 1 to 12, 1 to 11, 1 to 10, 1 to 9, 1 to 8, 1 to 7, 1 to 6, 1 to 5, 1 to 4, 1 to 3, or 1 to 2. In one embodiment, the number of carbon atoms of the alkyl group for $R^1$ to $R^4$ are independently 1, 2, 3, 4, 5, 6, 7, 8, 9, 10, 11, or 12. The less the number of carbon atoms of the alkyl group is, the more the heat resistance increases. In particular, the number of carbon atoms of the alkyl group is preferably 1 to 6.

In one embodiment, when the number of carbon atoms is 3 or more, the alkyl group for $R^1$ to $R^4$ are independently linear or branched. The linear alkyl group for $R^1$ to $R^4$ further increases the conductivity. The branched alkyl group for $R^1$ to $R^4$ increases the solubility in various solvents.

In one embodiment, when the alkyl group for $R^1$ to $R^4$ is a substituted alkyl group, specific examples of the substituent include a halogen group (halogen atom), $SR^5$ (S is a sulfur atom), $SeR^5$ (Se is a selenium atom), $OR^5$ (O is an oxygen atom), $SO_2R^5$ (S is a sulfur atom, and O is an oxygen atom), $PO_3R^5$ (P is a phosphorus atom, and O is an oxygen atom), an aryl group including 6 to 22 ring carbon atoms, and the like. Specific examples of the halogen group include F (fluorine atom), Cl (chlorine atom), Br (bromine atom), and I (iodine atom). $R^5$ is H (hydrogen atom), an alkyl group including 1 to 12 carbon atoms, or an aryl group including 6 to 22 ring carbon atoms.

In one embodiment, for the aryl group for $R^1$ to $R^4$, the explanations given for the aryl group in $Y^1$ is referred to.

In one embodiment, $Z^1$ and $Z^2$ are independently $Y^2R^1$, wherein $Y^2$ is S (sulfur atom) or Se (selenium atom), and $R^1$ is an alkyl group including 1 to 12 carbon atoms. In one embodiment, $Z^1$ and $Z^2$ are independently an alkylthio group including 1 to 12 carbon atoms or an alkylseleno group including 1 to 12 carbon atoms. Examples of the alkylthio group including 1 to 12 carbon atoms include a methylthio group and the like. Examples of the alkylseleno group including 1 to 12 carbon atoms include a methylseleno group and the like.

In one embodiment, $Z^1$ and $Z^2$ are the same as each other. This increases the thermal stability of the compound.

In one embodiment, the compound is represented by any one of the following formulas (E-4) to (E-16):

(E-4)

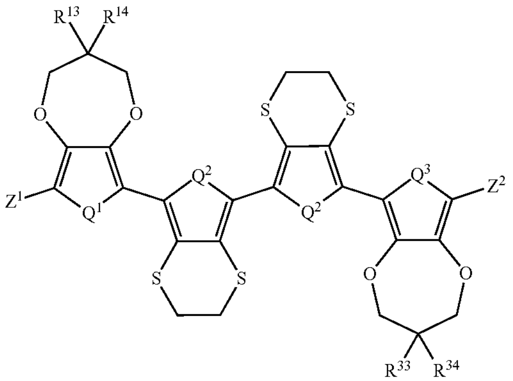

-continued
(E-5)
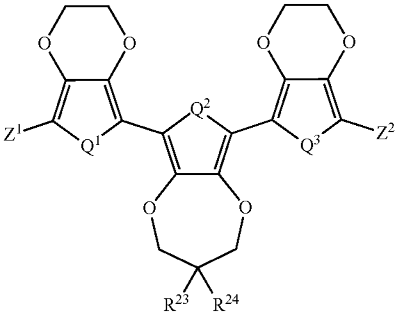
(E-6)
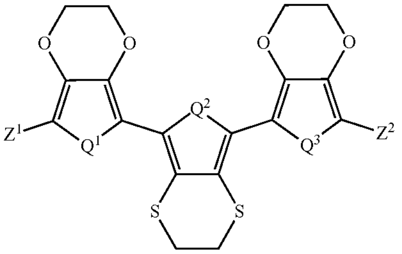
(E-7)
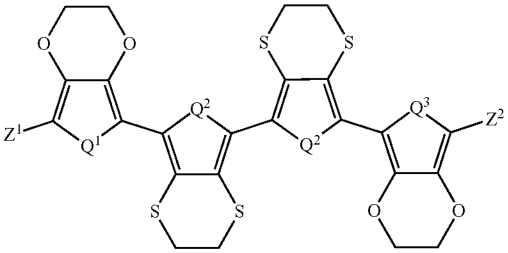
(E-8)
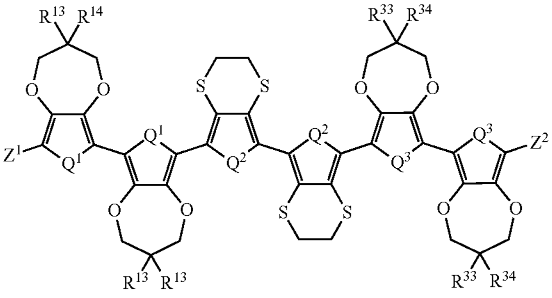
(E-9)
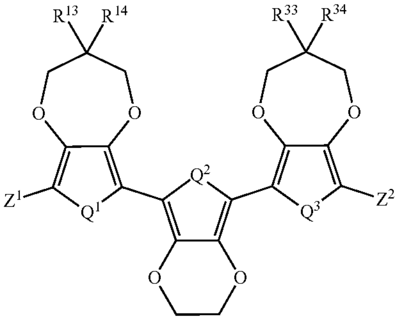
-continued
(E-10)
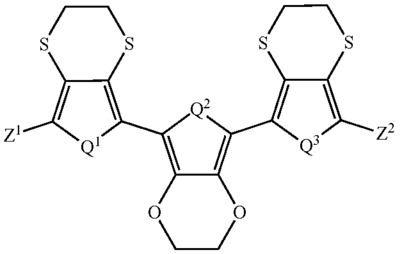
(E-11)
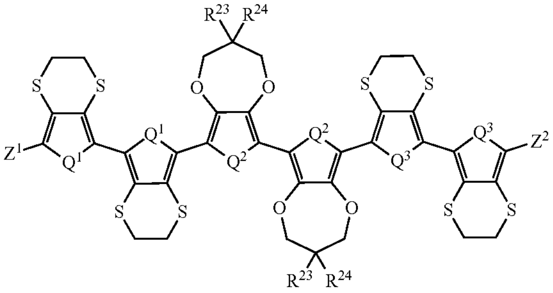
(E-12)
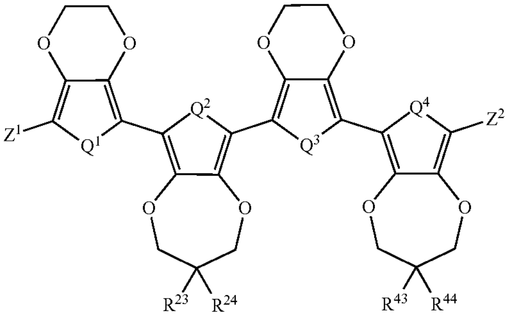
(E-13)
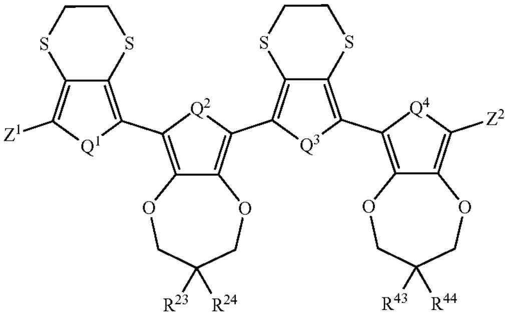
(E-14)
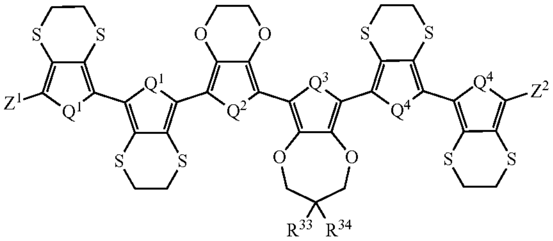

-continued (E-15)

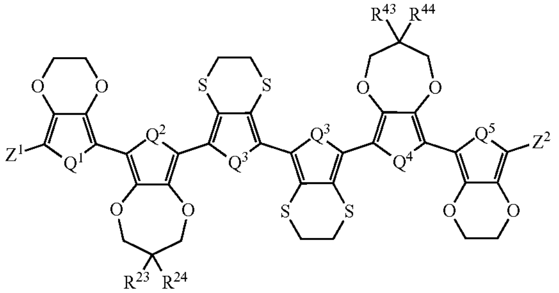

(E-16)

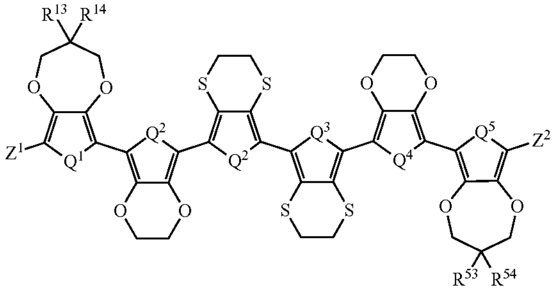

wherein in the formulas (E-4) to (E-16), $Q^1$ to $Q^5$, $R^{13}$, $R^{14}$, $R^{23}$, $R^{24}$, $R^{33}$, $R^{34}$, $R^{43}$, $R^{44}$, $R^{53}$, $R^{54}$, $Z^1$, and $Z^2$ are as defined in the formula (1).

In one embodiment, in the formulas (E-4) to (E-16), $Q^1$ to $Q^5$ are S.

In one embodiment in the formulas (E-4) to (E-16), $Q^1$ to $Q^5$ are S (sulfur atom);

$R^{13}$, $R^{14}$, $R^{23}$, $R^{24}$, $R^{33}$, $R^{34}$, $R^{43}$, $R^{44}$, $R^{53}$, and $R^{54}$ are independently an unsubstituted alkyl group including 1 to 12 carbon atoms;

$Z^1$ and $Z^2$ are independently $SR^1$ (S is a sulfur atom);

$R^1$ is a substituted or unsubstituted alkyl group including 1 to 12 carbon atoms.

In this embodiment, the number of carbon atoms of the alkyl group for $R^{13}$, $R^{14}$, $R^{23}$, $R^{24}$, $R^{33}$, $R^{34}$, $R^{43}$, $R^{44}$, $R^{53}$, $R^{54}$, and $R^1$ is independently 1, 2, 3, 4, 5, 6, 7, 8, 9, 10, 11, or 12, and when the number of carbon atoms is 3 or more, the alkyl group is linear or branched.

In one embodiment, in the formulas (E-4) to (E-16), $Q^1$ to $Q^5$ are Se (selenium atom).

In one embodiment, in the formulas (E-4) to (E-16), $Q^1$ to $Q^5$ are Se (selenium atom);

$R^{13}$, $R^{14}$, $R^{23}$, $R^{24}$, $R^{33}$, $R^{34}$, $R^{43}$, $R^{44}$, $R^{53}$, and $R^{54}$ are independently an unsubstituted alkyl group including 1 to 12 carbon atoms;

$Z^1$ and $Z^2$ are independently $SR^1$ (S is a sulfur atom);

$R^1$ is a substituted or unsubstituted alkyl group including 1 to 12 carbon atoms.

In this embodiment, the number of carbon atoms of the alkyl group for $R^{13}$, $R^{14}$, $R^{23}$, $R^{24}$, $R^{33}$, $R^{34}$, $R^{43}$, $R^{44}$, $R^{53}$, $R^{54}$, and $R^1$ is 1, 2, 3, 4, 5, 6, 7, 8, 9, 10, 11, or 12, and when the number of carbon atoms is 3 or more, the alkyl group is linear or branched.

In one embodiment, in the formulas (E-4) to (E-16), $Q^1$ to $Q^5$ are NH (N is a nitrogen atom and H is a hydrogen atom).

In one embodiment, in the formulas (E-4) to (E-16), $Q^1$ to Q are NH (N is a nitrogen atom, and H is a hydrogen atom);

$R^{13}$, $R^{14}$, $R^{23}$, $R^{24}$, $R^{33}$, $R^{34}$, $R^{43}$, $R^{44}$, $R^{53}$, and $R^{54}$ are independently an unsubstituted alkyl group including 1 to 12 carbon atoms;

$Z^1$ and $Z^2$ are independently $SR^1$ (S is a sulfur atom);

$R^1$ is a substituted or unsubstituted alkyl group including 1 to 12 carbon atoms.

In this embodiment, the number of carbon atoms of the alkyl group in $R^{13}$, $R^{14}$, $R^{23}$, $R^{24}$, $R^{33}$, $R^{34}$, $R^{43}$, $R^{44}$, $R^{53}$, $R^{54}$, and $R^1$ is independently 1, 2, 3, 4, 5, 6, 7, 8, 9, 10, 11, or 12, and when the number of carbon atoms is 3 or more, the alkyl group is linear or branched.

In one embodiment, the compound is represented by any one of the following formulas (4) to (34). In one embodiment, the compound is represented by any one of the formulas (4) to (8). The compounds represented by the formulas (4) to (11), (17), (20), and (23) to (34) correspond to the three-block form. The compounds represented by the formulas (12) to (14), (18), and (21) correspond to the four-block form. Furthermore, the compounds represented by the formulas (15), (16), (19), and (22) correspond to the five-block form.

(4)

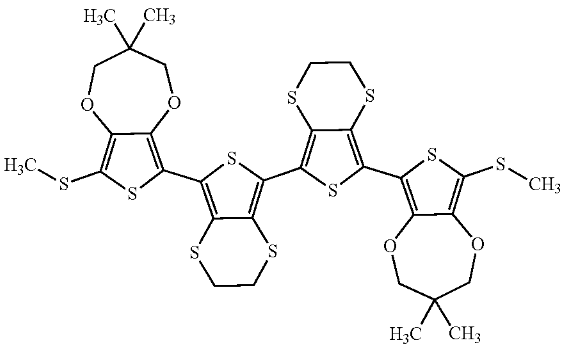

(5)

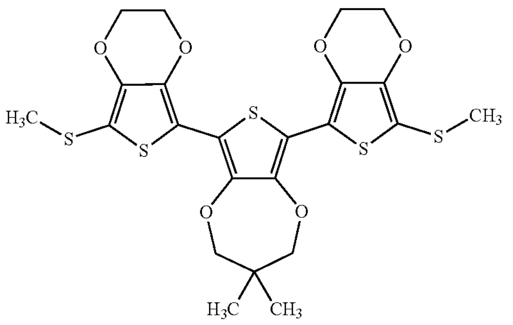

-continued
(6)
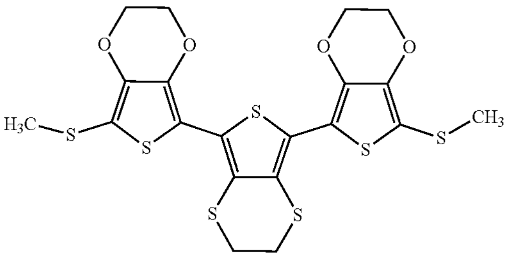
(7)
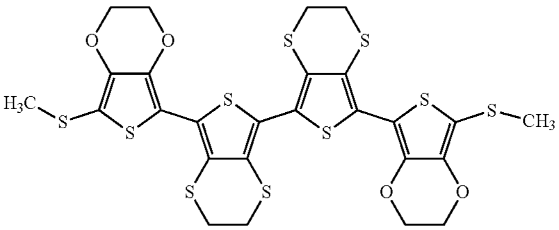
(8)
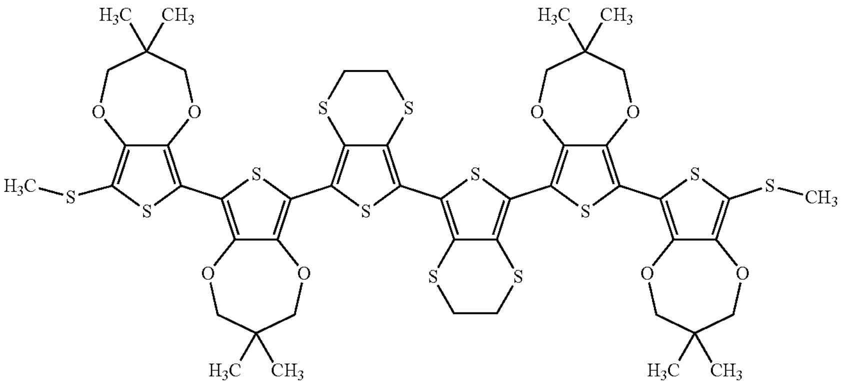
(9)
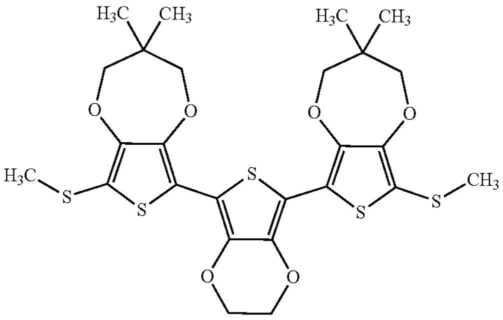
(10)
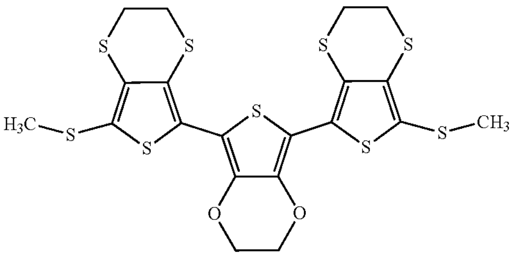
(11)
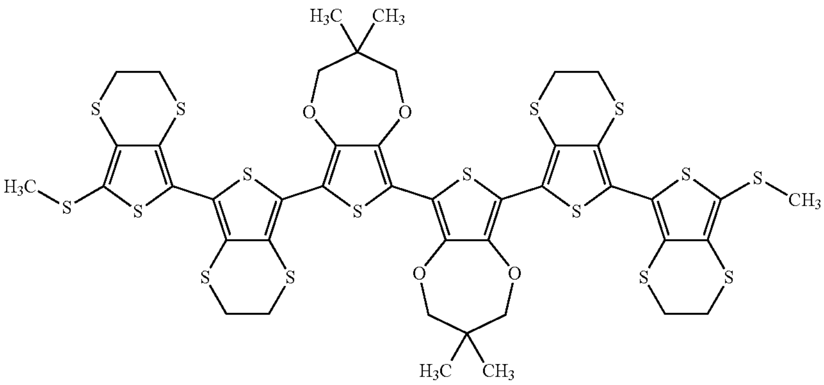

-continued
(12)
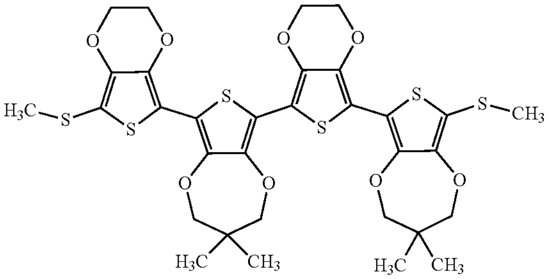
(13)
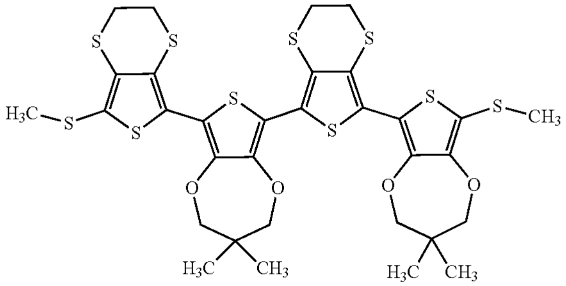
(14)
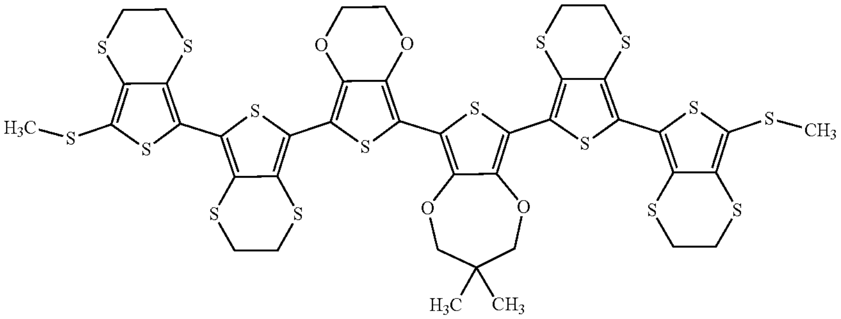
(15)
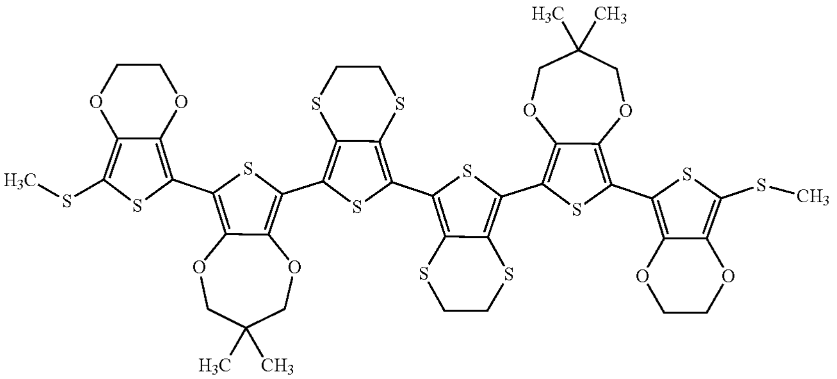
(16)
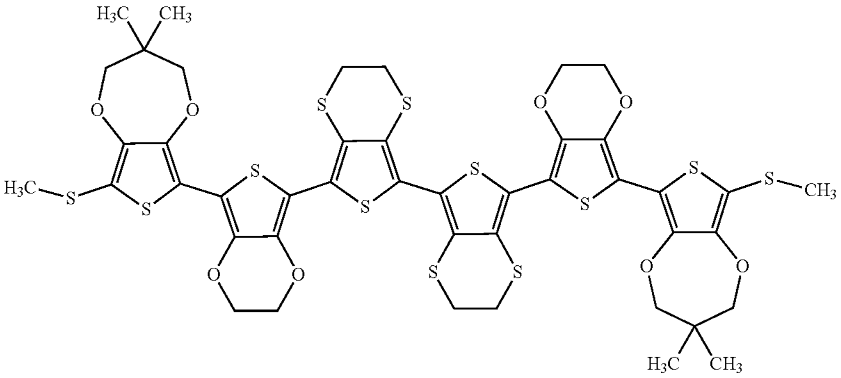

-continued
(17)
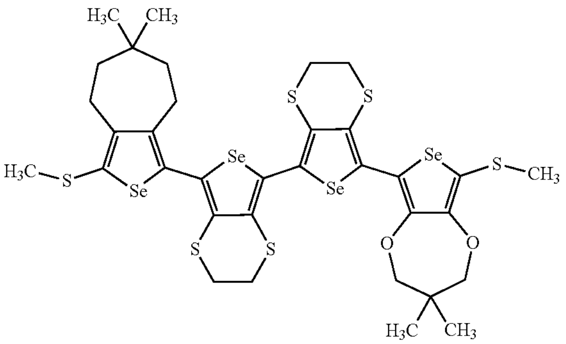
(18)
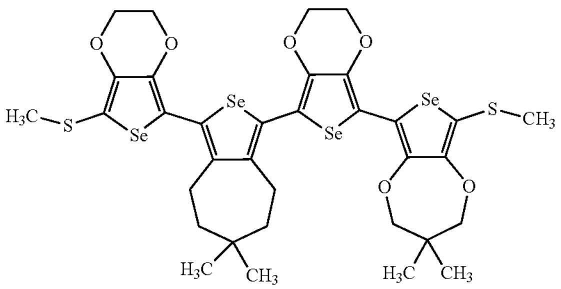
(19)
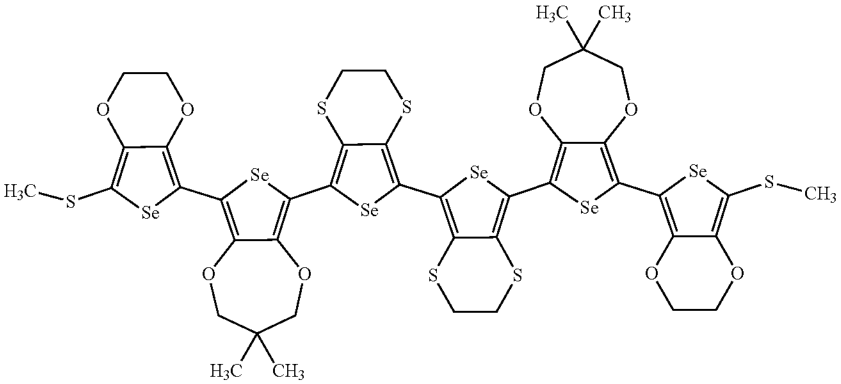
(20)
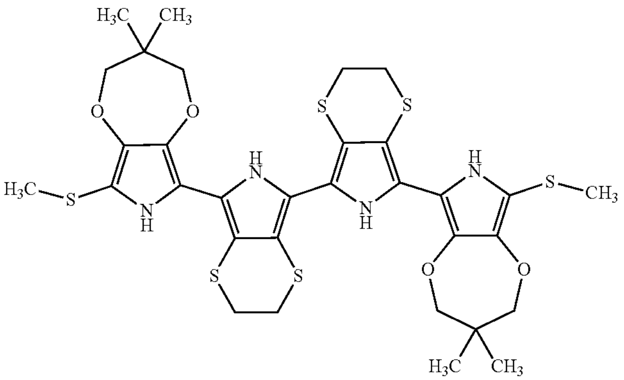
(21)
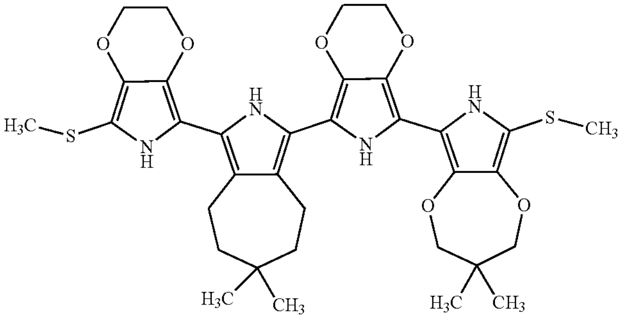

-continued
(22)
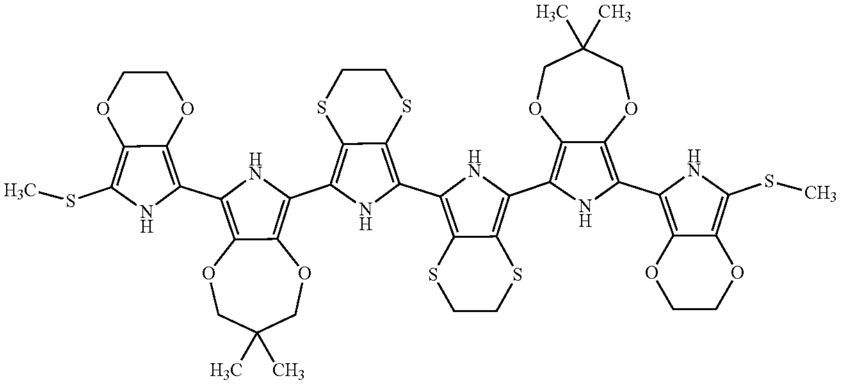
(23)
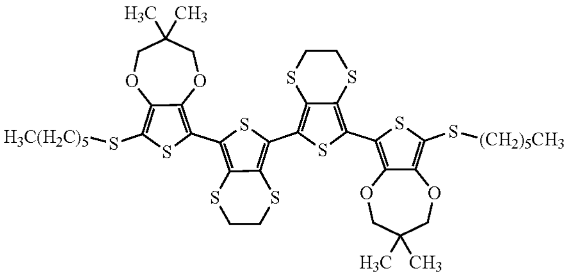
(24)
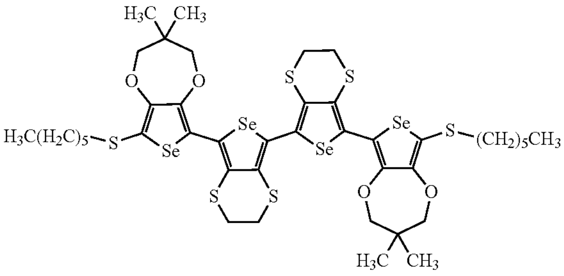
(25)
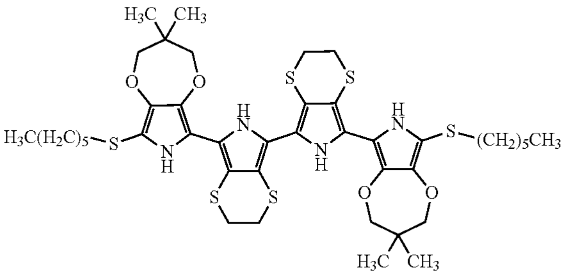
(26)
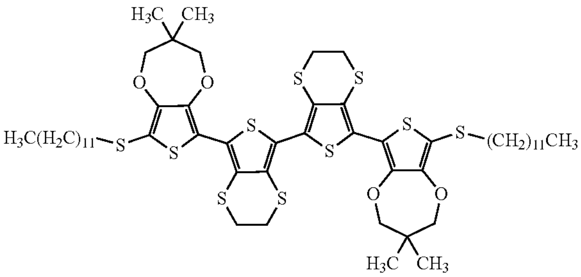
(27)
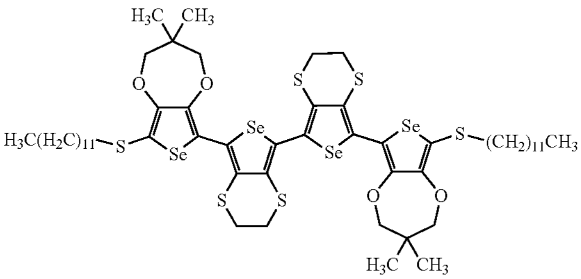
(28)
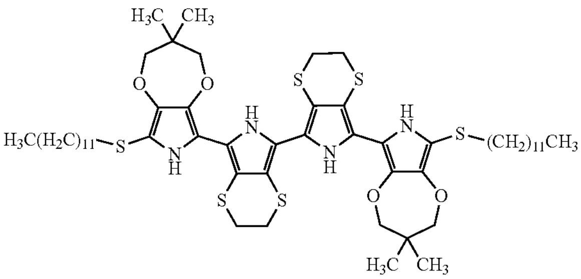

-continued (29)

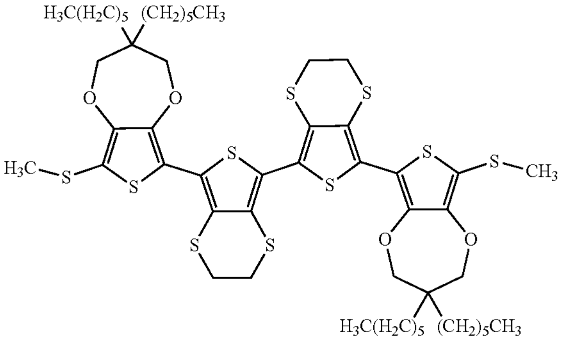

(30)

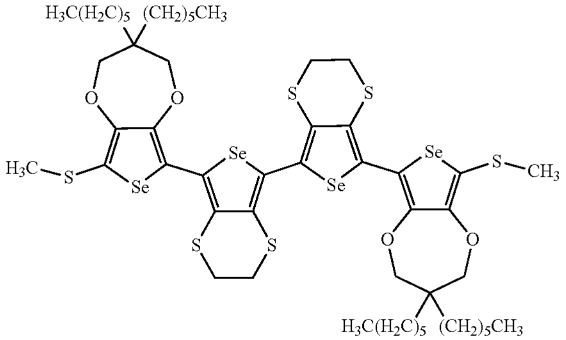

(31)

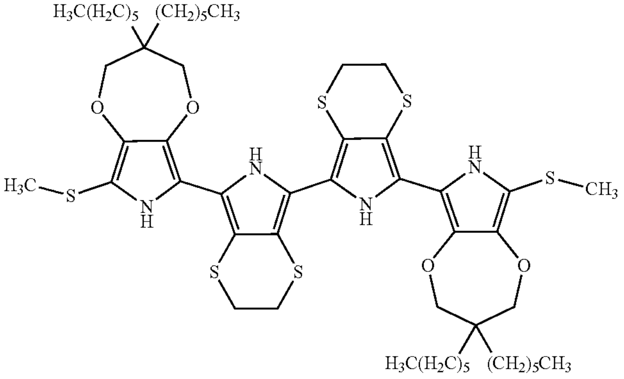

(32)

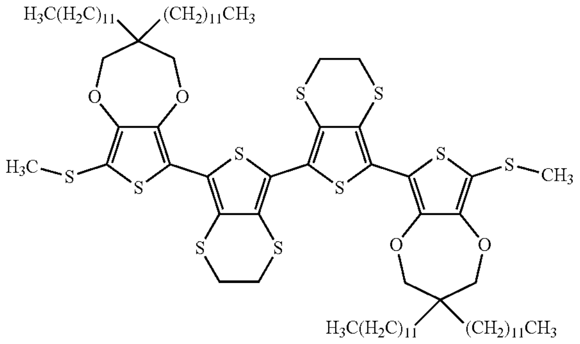

(33)

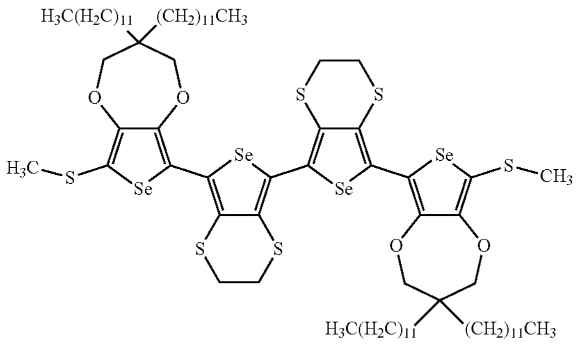

-continued (34)

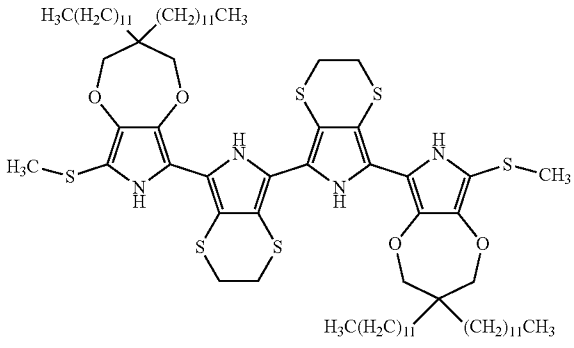

The compound according to an aspect of the invention is not limited to the compounds represented by the formulas (4) to (34) (hereinafter, also referred to as "specific example compounds"), and may be any compound represented by the formula (1). Needless to explain, the structure of each compound listed as specific example compounds may be partially modified within a range that the definitions of the formula (1) are satisfied. For example, a part of the structure of each compound listed as specific example compounds and a part of the structure of the compound shown as one embodiment can be appropriately combined. For example, in each compound listed as specific example compounds, a compound in which two methylthio groups are replaced with other groups defined as $Z^1$ and $Z^2$ is also a preferred specific example compound. Further, for example, in a compound having a unit represented by the formula (U3) among the specific example compounds, a compound in which two methyl groups in the unit are replaced with other groups defined as $R^3$ and $R^{74}$ is also a preferred specific example compound. Further, for example, in each compound listed as specific example compounds, a compound in which the number of each unit is changed within a range satisfying the definitions of the formula (1) is also a preferred specific example compound.

In one embodiment, the compound according to this aspect (assembly of the molecules represented by the formula (1)) has the same molecular weight in the proportion of 50% by mass or more, 60% by mass or more, 70% by mass or more, 80% by mass or more, 90% by mass or more, 95% by mass or more, 97% by mass or more, 99% by mass or more, 99.5% by mass or more, 99.7% by mass or more, 99.9% by mass or more, or substantially 100% by mass. The smaller the compound has the molecular weight distribution, the more preferable it is. The molecular weight distribution can be derived, for example, from the fad that each value of a, b, c, d, and e has a distribution. In addition, it is more preferable that the compound has no distribution of molecular weight (each value of a, b, c, d, and e has no distribution). This allows the compound to favorably form have an a suitable ordered arrangement and orientation, thereby further increasing conductivity.

The method of producing the compound according to this aspect is described in Examples, as an example.

2. Composition

The composition according to an aspect of the invention comprises the compound according to one aspect of the invention and a dopant.

The composition according to this aspect in which a dopant is added to the compound according to one aspect of the invention, and excellent conductivity is exhibited.

In this specification, the term "dopant" means an additive that when added to the compound according to one aspect of the invention, allows the composition including the compound to exhibit excellent conductivity.

The dopant is not particularly limited, and a conventionally known dopant may be used.

Preferable examples of the dopant include, for example, monovalent anionic species of TCNQ or $F_x$TCNQ (x is 2 or 4), halide ions such as a chloride ion, a bromide ion, and an iodide ion; polyhalide ions such as a triiodide ion; perhalide ions; a tetrafluoroborate ion; a hexafluoride arsenate ion; sulfate ions; nitrate ions; thiocyanate ions; a pentafluoric silicate ion; a hexafluoride silicate ion; phosphate ions such as a hexafluoride phosphate ion, a phenylphosphate ion, and a hexafluoride phosphate ion; a trifluoroacetate ion; alkylbenzenesulfonate ions such as a tosylate ion, an ethylbenzenesulfonate ion, and a dodecylbenzenesulfonate ion; alkylsulfonate ions such as a methylsulfonate ion, an ethylsulfonate ion, and a diisooctylsulfosuccinate ion; gallium chloride ions; cobalt chloride ions; polymeric ions such as a polyacrylate ion, a polyvinylsulfonate ion, a polystyrenesulfonate ion, and a poly(2-acrylamide-2-methylpropanesulfonate) ion; and the like. These may be used alone or in combination of two or more kinds.

More specifically, examples of the dopant include $LiCF_3SO_3$, $LiCF_3CO_2$, $LiAsF_9$, $LiSbF_6$, $LiAlCl_4$, LiCl, LiBr, $LiB(C_2H_5)_4$, $LiCH_3SO$, $LiC_4F_9SO_3$, $Li(CF_3SO_2)N$, and $Li[(CO_2)_2]_2B$, and the like.

In one embodiment, the dopant is one or more selected from the group consisting of $BF_4^-$, $ClO_4^-$, $PF_6^-$, $HSO_4^-$, $GaCl_4^-$, $CoCl_4^{2-}$, $SbF_6^-$, $SCN^-$, $Cl^-$, $Br^-$, $I^-$, $Br_3^-$, $I_3^-$, a monovalent anionic species of TCNQ, and a monovalent anionic species of $F_x$TCNQ (x is 2 or 4). This further increases the conductivity. In this specification, "TCNQ" means tetracyanoquinodimethane.

In one embodiment, the dopant is one or more selected from the group consisting of $BF_4^-$, $ClO_4^-$, $PF_6^-$, $HSO_4^-$, $GaCl_4^-$, $CoCl_4^{2-}$, $SbF_6^-$, $SCN^-$, $Cl^-$, $Br^-$, $I^-$, $Br_3^-$, $I_3^-$, monovalent anionic species of TCNQ or $F_x$TCNQ (x is 2 or 4). By the use of these, the conductivity is further increased.

The percentage of the proportion of the total number of moles of the dopant (counter anion) to the total number of moles of the unit α, the unit β, and the unit γ constituting the compound according to one aspect of the invention (also referred to as a "doping ratio") is not particularly limited.

In one embodiment, the doping ratio is 6 to 120% or 10 to 100%. This further increases the conductivity.

In one embodiment the composition comprises components other than the compound according to one aspect of the invention and the dopant Here, the other components are not particularly limited, and one or more components may be appropriately selected depending on the purpose and use. The other components may also be the solvent used in the preparation of the composition. Solvents are not particularly limited and examples thereof include acetone, acetonitrile, chloroform, methylene chloride, ethanol, methanol, chlorobenzene, o-dichlorobenzene, nitrobenzene, tetrachloroethane, tetrahydrofuran, water, and the like.

In one embodiment, 10% by mass or more, 20% by mass or more, 30% by mass or more, 40% by mass or more, 50% by mass or more, 60% by mass or more, 70% by mass or more, 80% by mass or more, 90% by mass or more, 95% by mass or more, 97% by mass or more, 99% by mass or more, 99.5% by mass or more, 99.7% by mass or more, 99.9% by mass or more, or substantially 100% by mass of the composition is occupied by the compound according to one aspect of the invention and the dopant, or the compound according to one aspect of the invention, the dopant, and the solvent. In the case of "substantially 100% by mass," inevitable impurities may be contained in the composition.

In one embodiment, the composition contains a single crystal structure constituted by the compound according to one aspect of the invention and the dopant.

In one embodiment, in the single crystal structure, the compounds according to one aspect of the invention are r-laminated to each other with equal intervals while being inclined.

In one embodiment, the composition has the electrical resistivity ρ at 25° C. of $10^5$ Ωcm or lower, $10^4$ Ωcm or lower, lower than $4.4\times10^3$ Ωcm, $4.3\times10^3$ Ωcm or lower, $10^3$ Ωcm or lower, $10^2$ Ωcm or lower, 10 Ωcm or lower, 1 Ωcm or lower, or $10^{-1}$ Ωcm or lower. The composition preferably has the electrical resistivity ρ at 25° C. of $10^{-1}$ Ωcm or or. The lower limit is not particularly limited, and is, for example, $1.7\times10^{-6}$ Ωcm or higher.

The electrical resistivity ρ at 25° C. is a value measured by the method described in Examples.

In one embodiment, the composition has the activation-energy $E_a$ at 0° C. of 300 meV or lower, 250 meV or lower, 200 meV or lower, 165 meV or lower, or 150 meV or lower. In addition, it is preferable that the activation-energy $E_a$ at 0° C. is 150 meV or lower. The lower limit is not particularly limited, and the activation-energy disappears at the stage of changing to metal conduction, and the electric resistance increases with temperature increasing.

The activation-energy $E_a$ at 0° C. is measured by the method described in Examples.

The composition according to this aspect is produced by the method described in Examples, as an example.

In one embodiment, a method of producing the composition has a step of adding a dopant to the compound according to this aspect, and optionally other steps.

The application of the compound according to an aspect of the invention and the composition according to an aspect of the invention is not particularly limited.

The compound according to an aspect of the invention and the composition according to an aspect of the invention are excellent in conductivity, therefore they are very useful for various applications requiring high conductivity, for example, as electrodes such as a condenser electrode, a transparent electrode, a battery electrode, a capacitor electrode, and the like, and as a conductive aid for an electrode and the like.

3. Conductive Aid

The conductive aid according to an aspect of the invention contains the composition according to one aspect of the invention.

The conductive aid according to this aspect is excellent in conductivity.

In one embodiment, by blending the conductive aid according to this aspect and other components for constituting a conductor, it is possible to form a conductor having excellent conductivity. Here, the conductor is not particularly limited, and may be, for example, an electrode and the like.

4. Electrode

The electrode according to an aspect of the invention is an electrode produced using any of the composition according to one aspect of the invention and the conductive aid according to one aspect of the invention.

The electrode according to this aspect is excellent in conductivity.

In one embodiment, the composition according to one aspect of the invention or the conductive aid according to one aspect of the invention may be applied to any substrate and cured as necessary to form an electrode. Here, the substrate itself may or may not have conductivity.

The application of the electrode according to this aspect is not particularly limited.

In one embodiment, the electrode is a condenser electrode, a transparent electrode, a battery electrode, or a capacitor electrode.

5. Laminated Body

The laminated body according to an aspect of the invention contains:

a substrate, and a layer containing the composition according to one aspect of the invention laminated on the substrate.

In the laminated body according to this aspect, the layer containing the composition according to one aspect of the invention is excellent in conductivity and functions well as a conductive layer.

In one embodiment, the composition according to one aspect of the invention can be applied to any substrate and optionally cured to form a layer containing the composition according to one aspect of the invention. Here, the substrate itself may or may not have conductivity.

EXAMPLES

Examples of the invention will be described below, but the invention is not limited to these Examples.

The outlines of measurement methods carried out in the following examples are as follows:

Gel permeation chromatography (GPC) was performed using a preparative HPLC (LC-908, manufactured by Japan Analytical Industry Co., Ltd.) equipped with a high-performance preparative GPC column (polystyrene column, 20 mmφ×(600+600) mm) (JAIGEL-1HR,-2HR, manufactured by Japan Analytical Industry Co., Ltd.).

Proton ($^{1}H$) and carbon ($^{13}C$) nuclear magnetic resonance (NMR) spectra were measured using a JEOL JNM-AL300 ($^{1}H$: 300 MHz; $^{13}C$: 75 MHz) spectrometer. $^{1}H$ NMR and $^{13}C$ NMR spectra measured in $CDCl_3$ were corrected for the solvent absorption.

Mass spectrometry was carried out using a JEOL JMS-AX500 (FD probe, positive mode) mass spectrometer.

The "room temperature" in the following Examples represents 25° C.

1. Synthesis of Compound and Preparation of Composition

Example 1

Synthesis of Compound

A compound (2MeS-4PS) represented by the following formula (4) was synthesized.

(4)

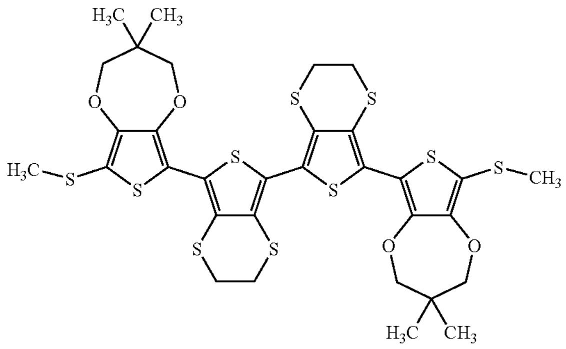

The synthetic scheme are as follows:

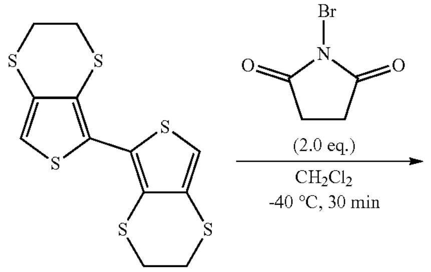

2H-2S

-continued

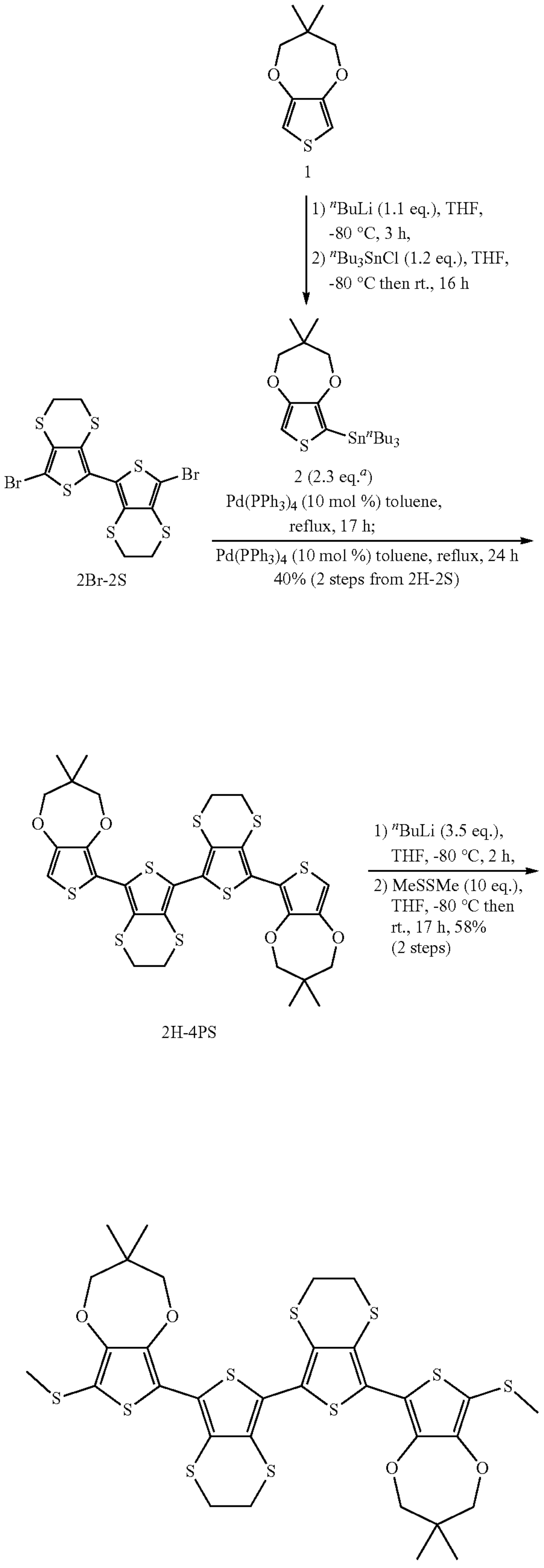

1

2Br-2S 2H-4PS

2MeS-4PS

The details are as follows:

Synthesis of Ethylenedithiothiofene-Type Dimer (2Br-2S)

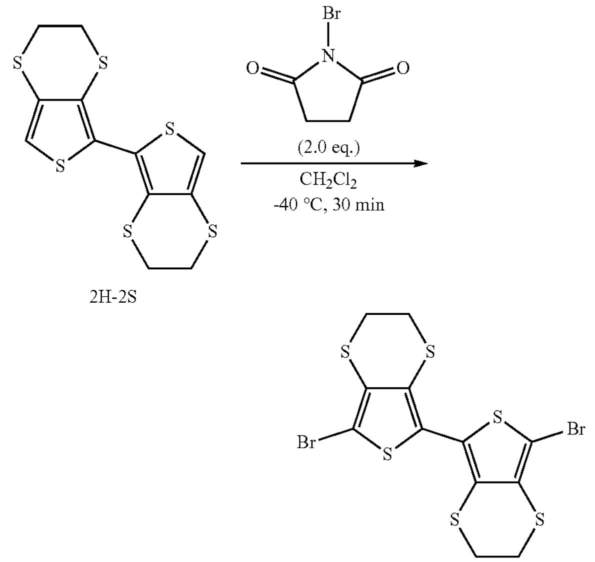

2H-2S

2Br-2S

Two two-necked eggplant-type flasks (reaction vessel) with a volume of 50 mL were prepared, and a stirrer was placed in each flask. The flasks were sealed with a septum, and heated the wall surface thereof with a heat gun for about 1 minute while being evacuated with a vacuum pump, to remove moisture. Then, the atmosphere inside the reaction vessel was replaced with argon. This procedure was repeated three times. The septum was opened under argon flow in one two-necked eggplant-type flask, and 300 mg of bis(3,4-ethylenedithiophene) (2H-2S) was added to the two-necked eggplant-type flask (reaction vessel), and the flask was capped with a septum. 30 mL of dichloromethane (manufactured by FUJIFILM Wako Pure Chemical Corporation, super-dehydrated) was added to the reaction vessel with a syringe, and the reaction vessel was cooled to −40° C. with stirring with a magnetic stirrer. In another two-necked eggplant-type flask, 309 mg of N-bromosuccinimide (manufactured by FUJIFILM Wako Pure Chemical Corporation) was placed and 7.5 mL of dichloromethane (manufactured by FUJIFILM Wako Pure Chemical Corporation, super-dehydrated) was placed with syringe, and the reaction vessel was cooled to 0° C. Then, a dichloromethane suspension of N-bromosuccinimide (manufactured by FUJIFILM Wako Pure Chemical Corporation) was added to a dichloromethane solution of 2H-2S using a cannula, and the mixture was stirred at −40° C. for 30 minutes. Then, a saturated aqueous sodium bicarbonate solution (30 mL) was added to the reaction solution, followed by washing with dichloromethane (30 mL) three times. To the washed organic layer, 0.2 M aqueous solution of sodium thiosulfate (60 mL) was added, and the reaction solution was stir ed for 30 minutes. Extraction with dichloromethane (30 mL) was then performed for the reaction solution three times. $Na_2SO_4$ was added to the mixed organic layer, and the mixture was stirred for about 30 minutes to remove moisture, and then the solids were removed. The resulting solution was concentrated with a rotary evaporator to obtain 2Br-2S (crude product 483 mg). 2Br-2S was not further purified, and 400 mg thereof was used for the subsequent synthesis of 2H-4PS.

Synthesis of Propylenedioxythiophene-Type Monomer 2

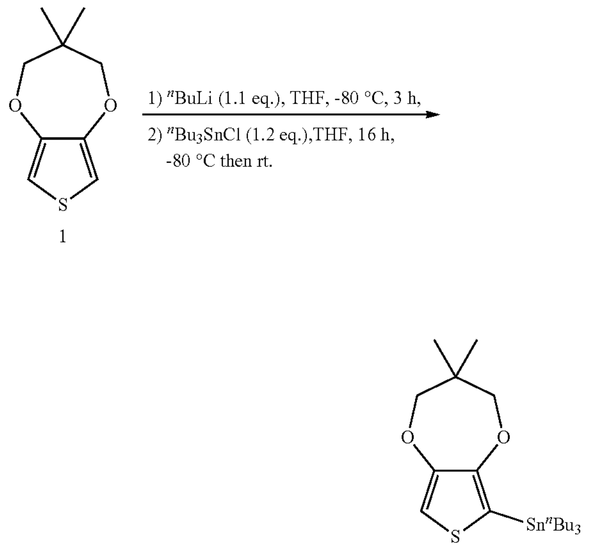

1

2

Two two-necked eggplant-type flasks (reaction vessel) with a volume of 50 mL were prepared, and a stirrer was placed in each flask. The flasks were sealed with a septum, and heated the wall surface thereof with a heat gun for about 1 minute while being evacuated with a vacuum pump, to remove moisture. Then, the atmosphere inside the reaction vessel was replaced with argon. This procedure was repeated three times. The septum was opened under argon flow in one two-necked eggplant-type flask, and, and 342 mg of propylene-type monomer 1 was placed in the flask and the flask was capped with a septum. 6 mL of THF (manufactured by FUJIFILM Wako Pure Chemical Corporation, super-dehydrated, containing stabilizer) was placed in the reaction vessel with a syringe, and the reaction mixture was cooled to −80° C. while stirring with a magnetic stirrer. 1.44 mL of r-BuLi (1.6 M in r-hexane) (manufactured by Kanto Chemical Co., Inc.) was added gradually dropwise into the reaction solution with a syringe over a period of 5 minutes. The reaction solution was continued to stir at −80° C. for 3 hours, and 601 μL of tri(n-butyl)tin was placed in the reaction vessel using a syringe. Stirring was continued for 17 hours while raising the temperature of the reaction solution to room temperature. The reaction solution was filtered through Celite and washed with dichloromethane (manufactured by FUJIFILM Wako Pure Chemical Corporation) (20 mL), and the solvent of the mixed solution was distilled off using a rotary evaporator to obtain propylenedioxythiophene monomer 2 (crude product 1.00 g). This monomer 2 was not further purified and used directly for the subsequent reaction.

Synthesis of Unsubstituted Tetramer (2H-4PS)

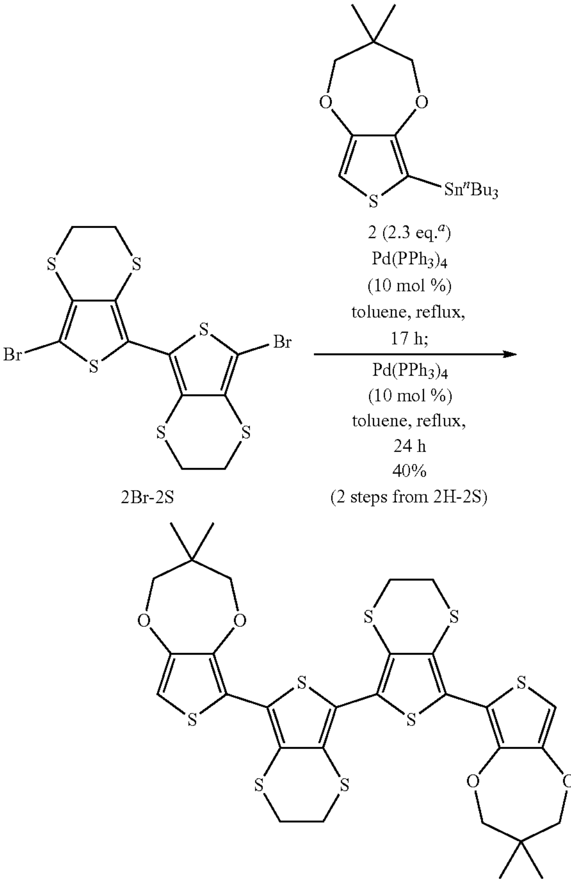

2Br-2S 2H-4PS

The septum of another two-necked eggplant-type flask was opened under argon flow, and 400 mg of 2Br-2S (crude product), total amount (1.00 g) of monomer 2 (crude product), and 91.7 mg of tetras(triphenylphosphine)palladium were placed in the flask, and the flask was capped with septum. 25 mL of toluene (manufactured by FUJIFILM Wako Pure Chemical Corporation) was added to the flask and the reaction solution was refluxed for 17 hours. Then, after cooling the reaction solution to room temperature, the septum was opened under argon flow, and 92.0 mg of tetrakis(triphenylphosphine)palladium was further added thereto, and the flask was capped with a septum. The reaction solution was refluxed for 24 hours, cooled to room temperature, and black solids were removed by Celite filtration, to obtain a crude product. The obtained crude product was purified using a preparative HPLC equipped with a high-performance preparative GPC column, followed by reprecipitation using dichloromethane as a good solvent and hexane as a poor solvent to obtain 2H-4PS as 223 mg of yellow powder. The total yield of the two steps from 2H-2S was 44%.

Physical property values: $^{1}$H-NMR ($CDCl_3$, 300 MHz) δ1.05 (s, 12H), 3.21 to 3.26 (m, 8H), 3.76 (s, 4H), 3.86 (s, 4H), 6.56 (s, 2H); $^{13}$C-NMR ($CDCl_3$, 75 MHz) δ 21.7, 28.2, 28.8, 39.1, 80.1, 80.4, 105.3, 115.1, 123.8, 124.6, 127.1, 128.6, 146.9, 150.0.

Synthesis of Dimethylthiolated Tetramer (2H-4PS)

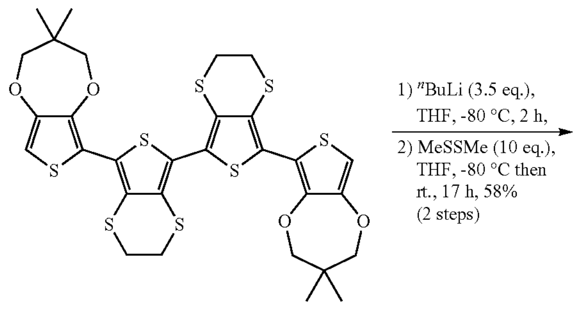

2H-4PS

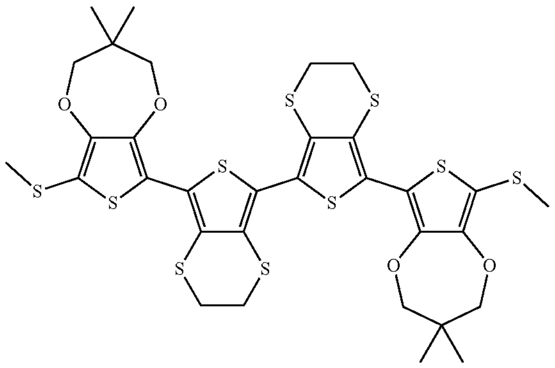

2MeS-4PS

In a Schenk-type flask (reaction vessel) with a volume of 10 mL, a stirrer was placed, sealed with a septum, and heated the wall surface thereof with a heat gun for about 1 minute while being evacuated with a vacuum pump, to remove moisture. Then, the atmosphere inside the reaction vessel was replaced with argon. This procedure was repeated three times. The septum was opened under argon flow, 142 mg of 2H-4PS was placed in the flask, and the flask was capped with a septum. 3 mL of THF (manufactured by FUJIFILM Wako Pure Chemical Corporation, super-dehydrated, containing stabilizer) was added to the reaction vessel with a syringe, and the reaction vessel was cooled to −80° C. while stirring with a magnetic stirrer. 0.45 mL of n-BuLi (1.6 M in n-hexane (manufactured by Kanto Chemical Co., Inc.) was added gradually dropwise into the reaction solution with a syringe over a period of 1 minutes. The reaction solution was continued to stir at −80° C. for 2 hours, and 0.18 mL of dimethyldisulfide (manufactured by FUJIFILM Wako Pure Chemical Corporation) was added to the reaction vessel using a syringe, and stirring was continued for 17 hours while raising the temperature of the reaction solution to room temperature. After the solvent were removed by vacuum pump, a saturated aqueous sodium bicarbonate solution (6 mL) was added to the reaction solution, followed by extraction with dichloromethane (20 mL) three times. $Na_2SO_4$ was added to the mixed organic layer, and the mixture was stirred for about 30 minutes to remove moisture, and then the solids were filtered off and the resulting solution was concentrated by a rotary evaporator to obtain crude product. The resulting crude product was purified using a preparative HPLC equipped with high-performance preparative GPC column to finally obtain 2MeS-4PS (a compound represented by the formula (4)) from 2H-4PS as a yellow powder in 58% yield as a two-step total yield.

Physical property values: $^{1}$H-NMR ($CDCl_3$, 300 MHz) δ 1.07 (s, 12H), 2.43 (s, 6H), 3.21 to 3.27 (m, 8H), 3.88 (s, 4H), 3.88 (s, 4H); $^{13}$C-NMR ($CDCl_3$, 75 MHz) δ 21.8, 28.2, 28.8, 39.1, 80.1, 80.4, 105.3, 115.1, 123.8, 124.6, 127.1, 128.6, 146.9, 150.0.

Preparation of Composition 1 (Electrolytic Oxidation Method)

1.0 mg of the compound represented by the formula (4) was added to the oxidized side of the H-type cell for electrolytic oxidation. To both sides of the cell, 18 mg of n-$Bu_4NPF_6$ (manufactured by Sigma-Aldrich Co. LLC) was added as a dopant source, and 18 mL of acetone (manufactured by FUJIFILM Wako Pure Chemical Corporation, super-dehydrated) was slowly added while being run down on the wall surface of the cell. To platinum electrodes of the cell, a current of 0.25 μA was applied in a thermostat at 50° C., allowing the cell to stand for 4 days, and then separating the precipitated glossy rod-shaped red crystal from the solution by filtration, to obtain Composition 1. As a result of the single crystal structure analysis, the doping ratio was 50%.

Preparation of Composition 2 (Chemical Oxidation Method)

A composition was prepared by diffusion method. Specifically, in a 6 mL vial, 2.0 mg of the compound represented by the formula (4) and 0.6 mg of $F_2$TCNQ (manufactured by Tokyo Chemical Industry Co., Ltd.) as a dopant source were placed and mixed, and 6 mL of dichloromethane (manufactured by FUJIFILM Wako Pure Chemical Corporation, reagent special grade) was added thereto. After mixing, the solution mixture was allowed to stand for 3 days for concentration and solvent evaporation, to obtain a composition Composition 2. As a result of the single crystal structure analysis, the doping ratio was 50%.

Example 2

Synthesis of Compound

The compound represented by the following formula (5) (2MeS-3OP) was synthesized.

(5)

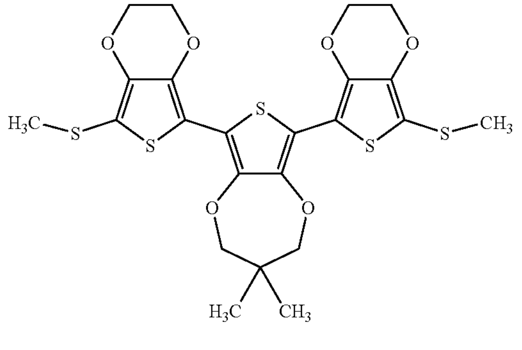

The synthetic scheme is as follows:

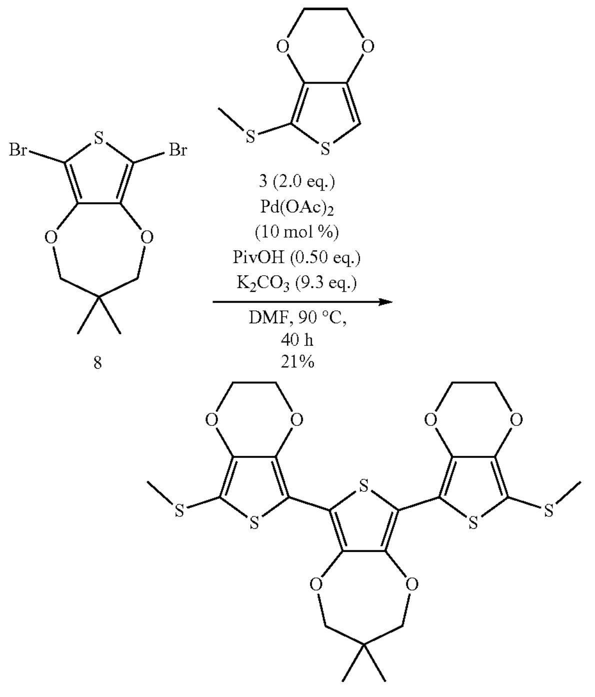

2MeS-3OP

The details are as follows:

A stirrer and 99.0 mg of methylthiolated ethylenedioxythiophene-type monomer 3, 89.2 mg of dibrominated propylenedioxy-type monomer 8, 5.9 mg of palladium acetate (II), and 336 mg of potassium carbonate were placed in a screw-capped vial (reaction vessel) with a volume of 6 mL, and the vial was brought into a nitrogen-substituted glove box 13.1 mg of pivallic acid was added to the screw-capped vial (reaction vessel) in a glove box, and then 5 mL of dimethylformamide (manufactured by FUJIFILM Wako Pure Chemical Corporation, super-dehydrated) was added to the reaction vessel, and the screw cap were closed. The reaction vessel was heated up to 90° C. with stirring by a magnetic stirrer on a staged hot plate and stirred at that temperature for 40 hours. Then, the reaction solution was cooled to room temperature, and diluted with 50 mL of dichloromethane (manufactured by FUJIFILM Wako Pure Chemical Corporation, reagent special grade), and the organic layer was washed once each with 50 mL of water and a saturated aqueous sodium thiosulfate solution.

$Na_2SO_4$ was added to the organic layer washed by the liquid separation, and the organic layer was stirred for about 10 minutes to remove moisture, and then the solid was filtered off and the obtained solution was concentrated by a rotary evaporator to obtain a crude product. The crude product was purified by medium pressure column chromatography with an automated purification system (Biotage (registered trade name), Isorela One) using the following conditions (Biotage (registered trade name) SNAP Ultra 50 g, developing solvent n-hexane:$CH_2CH_2$=6:4 to 2:8), and the resulting crude product was further purified using a preparative HPLC equipped with a high-performance preparative GPC column to obtain 31 mg of yellow powder of 2MeS-3OP (a compound represented by the formula (5)) in a yield of 21%.

Physical property values: $^1$H-NMR ($CDCl_3$, 300 MHz) δ 1.11 (s, 6H), 2.39 (s, 6H), 3.85 (s, 4H), 4.323 (brs, 8H); MS (FD) calcd for $C_{23}H_{24}O_6S_5$ [M+.] 556.0, found 556.1.

Example 3

The compound represented by the following formula (6) (2MeS-3OS) was synthesized.

(6)

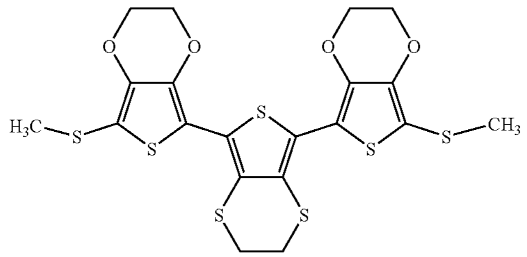

The synthetic scheme are as follows:

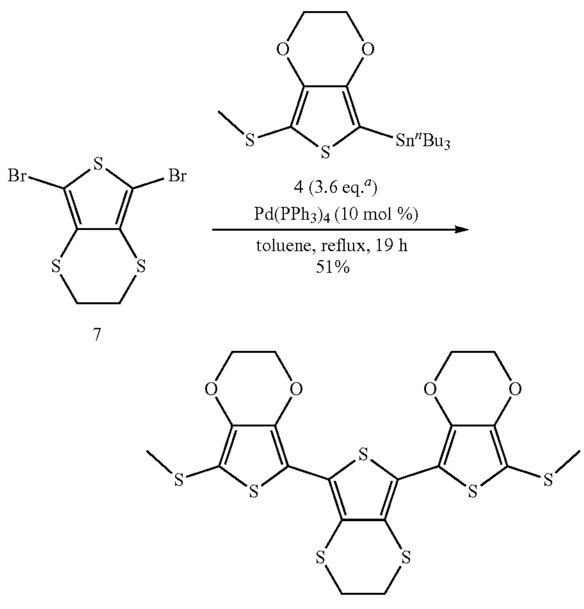

2MeS-3OS

The details are as follows:

A two-necked eggplant-type flask (reaction vessel) with a volume of 100 mL was prepared, and a stirrer was placed in the flask. The flask was sealed with a septum, and heated the wall surface thereof with a heat gun for about 1 minute while being evacuated with a vacuum pump, to remove moisture. Then, the atmosphere inside the reaction vessel was replaced with argon. This procedure was repeated three times. The septum of the two-necked eggplant-type flask was opened under argon flow, and 306 mg of dibrominated ethylenedithiophene-type monomer 7, the total amount of tri-n-butylstanylated ethylenedioxythiophene-type monomer 4 (crude product) synthesized from methylthiolated ethylenedioxythiophene-type monomer 3 (630 mg, 3.35 mmol), and 109 mg of tetrakis(triphenylphosphine)palladium were placed in the flask, and the flask was capped with the septum. 20 mL of toluene (manufactured by FUJIFILM Wako Pure Chemical Corporation) was added thereto, and the reaction mixture was refluxed for 17 hours. Then, after cooling the reaction mixture to room temperature, the septum was opened under argon flow, and 109.0 mg of tetrakis(triphenylphosphine) palladium was further added thereto, and the flask was capped with a septum. The reaction solution was refluxed for 19 hours, cooled to room temperature, and black solids were removed by Celite filtration, to obtain a crude product. The obtained crude product was purified using a preparative HPLC equipped with a high-performance preparative GPC column, followed by purification by reprecipitation using dichloromethane as a good solvent and hexane as a poor solvent, to obtain 255.3 mg (466.9 μmol) of 2MeS-3OS (a compound represented by the formula (6)) as a yellow powder in a yield of 51%.

Physical property values: $^1$H-NMR ($CDCl_3$, 300 MHz) δ 2.42 (s, 6H), 3.26 (s, 4H), 4.33 (s, 8H).

Example 4

The compound represented by the following formula (7) (2MeS-4OS) was synthesized.

(7)

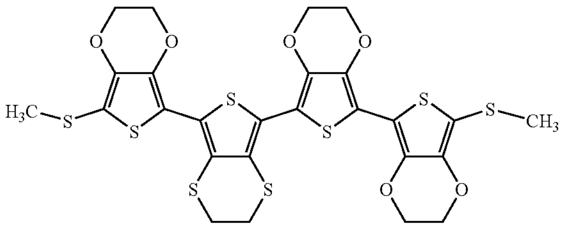

The synthetic scheme are as follows:

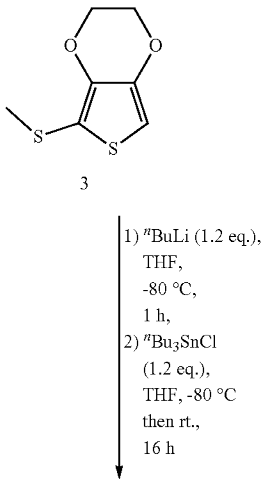

3

-continued

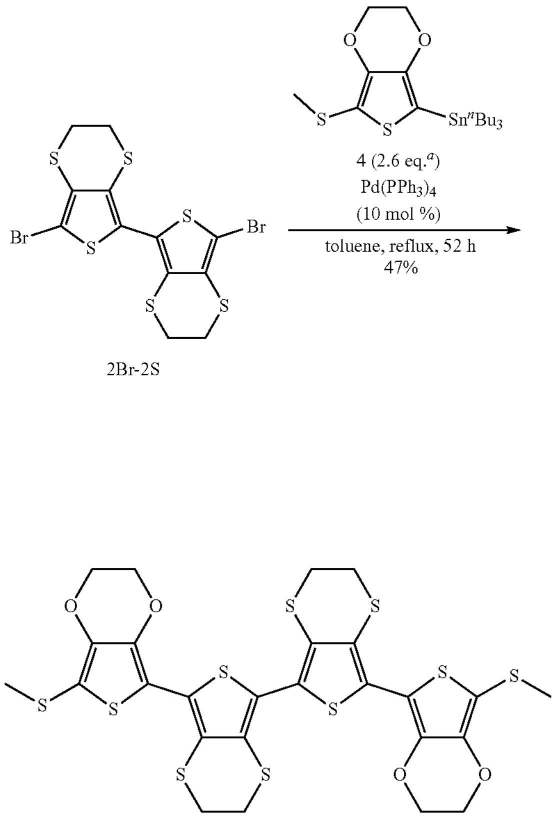

2Br-2S

2MeS-4OS

The details are as follows:

Synthesis of Tributylstannated Dioxythiophene-Type Monomer 4

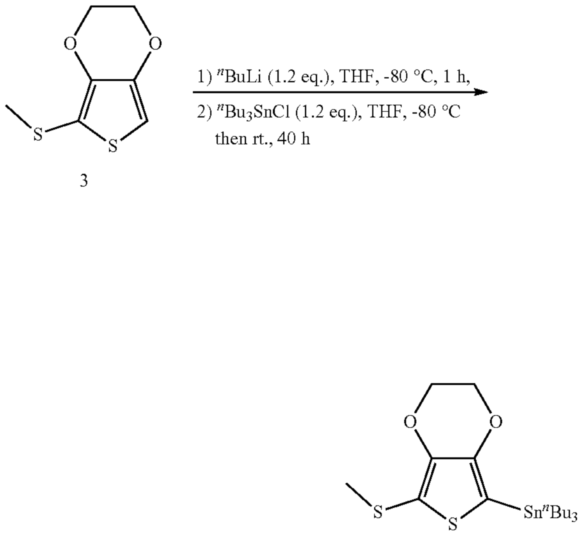

3

4

A Schlenk-type flask (reaction vessel) with a volume of 10 mL was prepared, a stirrer was placed therein. The flask was sealed with a septum, and heated the wall surface thereof with a heat gun for about 1 minute while being evacuated with a vacuum pump, to remove moisture. Then, the atmosphere inside the reaction vessel was replaced with argon. This procedure was repeated three times. The septum of one two-necked eggplant-type flask was opened under argon flow, and 82 mg of methylthiolated ethylenedioxythiophene-type monomer 3 was placed therein, and the flask was capped with the septum. 1.2 mL of THF (manufactured by FUJIFILM Wako Pure Chemical Corporation, super-dehydrated, containing stabilizer) was added to the reaction vessel with a syringe, and the reaction solution was cooled to −80° C. while stirring with a magnetic stirrer. 300 μL of n-BuLi (1.6 M in n-hexane (manufactured by Kanto Chemical Co., Inc.) was added gradually dropwise into the reaction solution with a syringe over a period of 5 minutes. The reaction solution was continued to stir at −80° C. for 1 hours, and 130 μL of tri(n-butyl)tin was added to the reaction vessel using a syringe. The reaction solution was continued to stir for 40 minutes while raising the temperature thereof to room temperature. The reaction solution was filtered through Celite and washed with dichloromethane (manufactured by FUJIFILM Wako Pure Chemical Corporation) (10 mL). The solvent was distilled off from the mixed solution by a rotary evaporator to obtain tributylstannated dioxythiophene-type monomer 4. This monomer 4 was not further purified and used directly for the subsequent reaction.

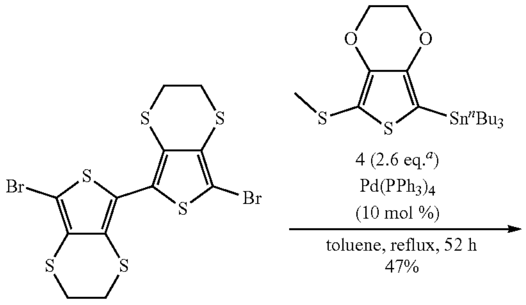

2Br-2S

-continued

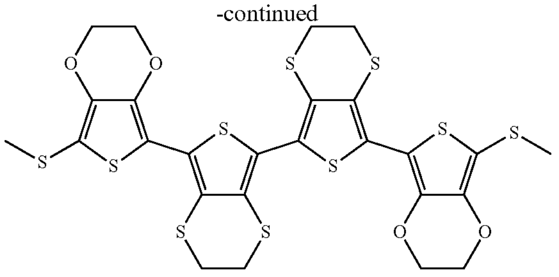

2MeS-4OS

A two-neck eggplant-type flask (reaction vessel) with a volume of 50 mL was prepared, and a stirrer was placed therein. The flask was sealed with a septum, and heated the wall surface with a heat gun for about 1 minute while being evacuated with a vacuum pump to remove moisture. The monomer 4 (the total amount of crude product) and 94 mg of 2Br-2S synthesized and isolated in the same manner as in Example 1, and 21.6 mg of tetrakis(triphenylphosphine) palladium were placed in the flask, and the flask was capped with septum. 5.5 mL of toluene (manufactured by FUJIFILM Wako Pure Chemical Corporation) was added thereto, and the reaction solution was refluxed for 52 hours. The reaction solution was cooled to room temperature, and black solids were removed by celite filtration, to obtain a crude product. The obtained crude product was purified using a preparative HPLC equipped with a high-performance preparative GPC column, followed by purification by reprecipitation using dichloromethane as a good solvent and hexane as a poor solvent to obtain 62.8 mg (87.3 μmol) of 2MeS-4OS (a compound represented by the formula (7)) as a yellow powder in a yield of 47%.

Physical property values: $^1$H-NMR ($CDCl_3$, 300 MHz) δ 2.42 (s, 6H), 3.22 to 329 (m, 8H), 4.32 (s, 8H).

Example 5

Synthesis of Compound

The compound (2MeS-6PS) represented by the following formula (8) was synthesized.

(8)

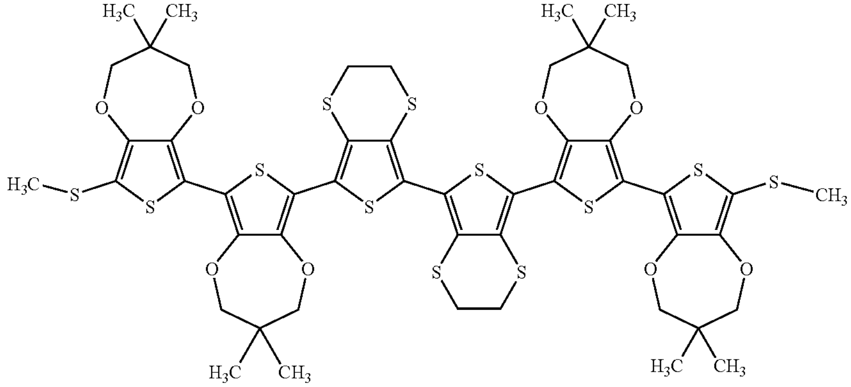

The synthetic scheme are as follows:
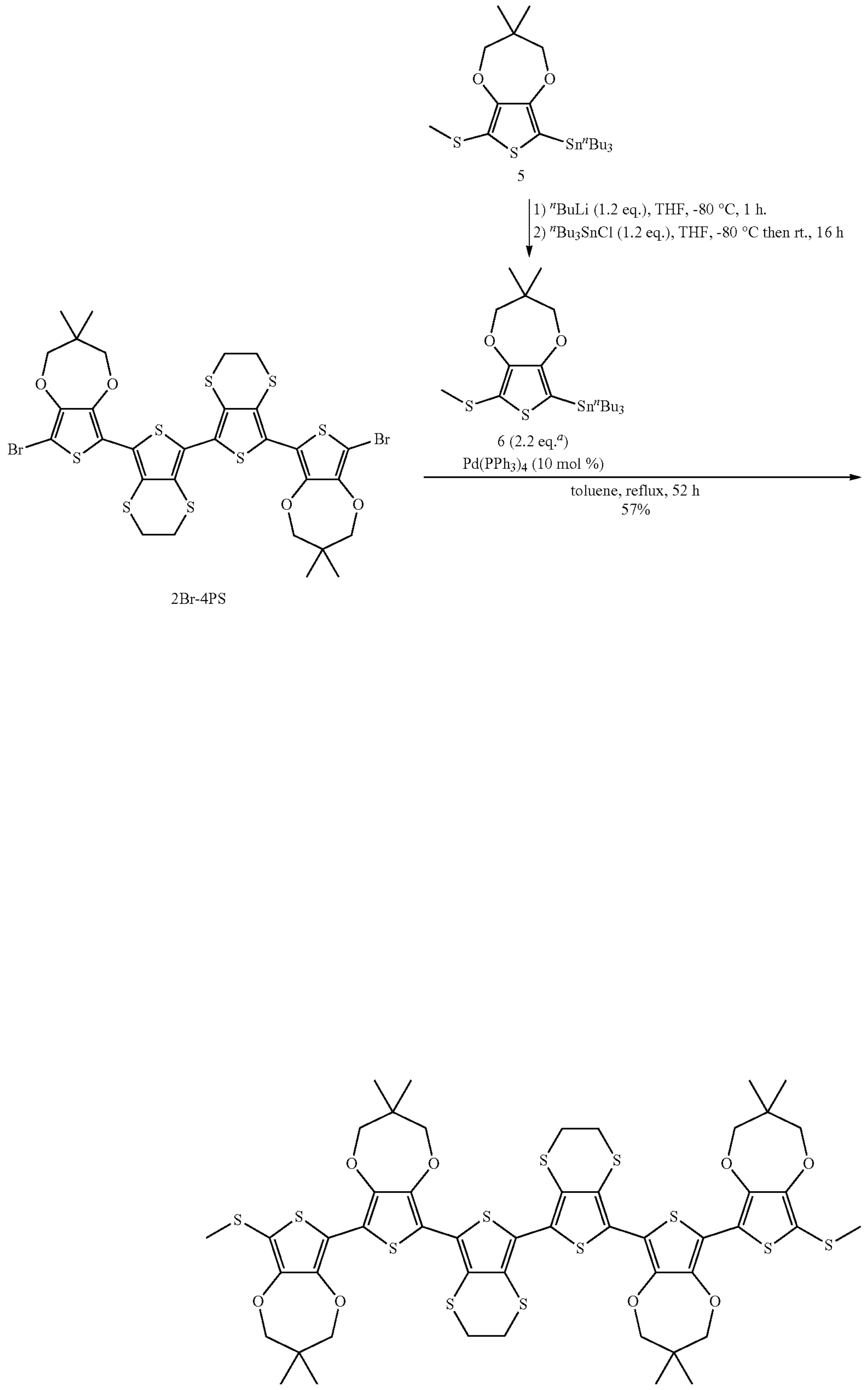
2MeS-6PS

The details are as follows:

Synthesis of Tri-n-Butylstanylated Propylenedioxy-Type Monomer 6

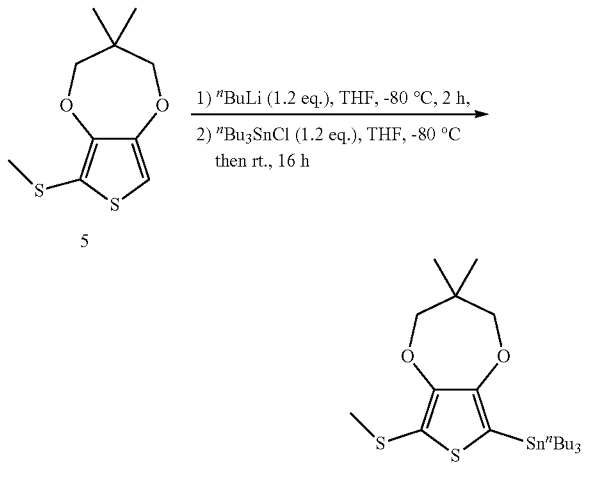

5

6

A Schlenk-type flask (reaction vessel) with a volume of 10 mL was prepared, and a stirrer was placed therein. The flask was sealed with a septum, and heated the wall surface thereof with a heat gun for about 1 minute while being evacuated with a vacuum pump, to remove moisture. Then, the atmosphere inside the reaction vessel was replaced with argon. This procedure was repeated three times. The septum of the flask was opened under argon flow, and 57 mg of methylthiolated propylenedioxy-type monomer 5 was placed therein, and the flask was capped with a septum. 2 mL of THF (manufactured by FUJIFILM Wako Pure Chemical Corporation, super-dehydrated, containing stabilizer) was added to the reaction vessel by a syringe, and the reaction mixture was cooled to −80° C. while stirring with a magnetic stirrer. 0.24 mL of n-BuLi (1.6 M in n-hexane (manufactured by Kanto Chemical Co., Inc.) was added gradually dropwise into the reaction solution by a syringe over a period of 1 minutes. The reaction solution was continued to stir at −80° C. for 2 hours, and 100 μL of tri(n-butyl)tin was added to the reaction vessel using a syringe. The reaction solution was continued to stir for 16 hours while raising the temperature thereof to room temperature. The reaction solution was filtered through Celite and washed with dichloromethane (manufactured by FUJIFILM Wako Pure Chemical Corporation) (10 mL). The solvent was distilled off from the mixed solution by a rotary evaporator to obtain tri-n-butylstanylated propylenedioxy-type monomer 6. This monomer 6 was not further purified and used directly for the subsequent reaction.

Synthesis of Dibrominated Tetramer (2Br-4PS)

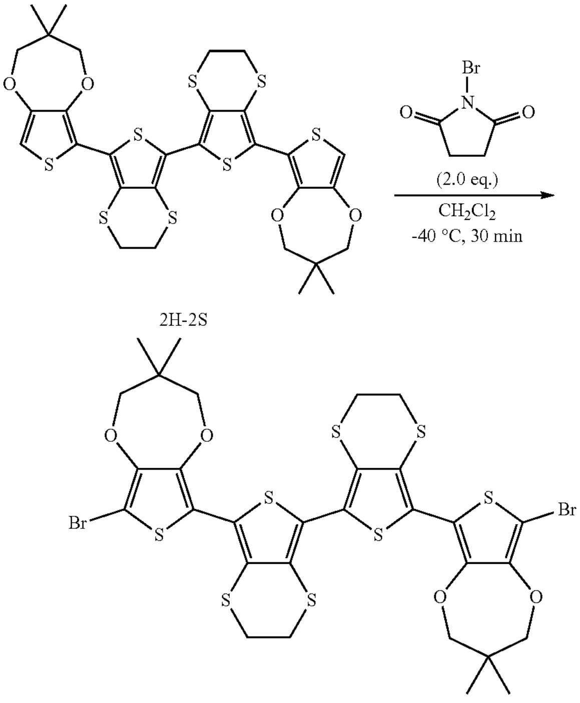

2H-2S

2Br-4PS

Two two-necked eggplant-type flasks (reaction vessel) with a volume of 50 mL were prepared, and a stirrer was placed in each flask. The flasks were sealed with a septum, and heated the wall surface thereof with a heat gun for about 1 minute while being evacuated with a vacuum pump to remove moisture. Then, the atmosphere inside the reaction vessel was replaced with argon. This procedure was repeated three times. The septum was opened under argon flow in one two-necked eggplant-type flask, and 83 mg of 2H-4PS was placed in the two-necked eggplant-type flask (reaction vessel), and the flask was capped with a septum. 8 mL of dichloromethane (manufactured by FUJIFILM Wako Pure Chemical Corporation, super-dehydrated) was added to the reaction vessel with a syringe, and the reaction mixture was cooled to −40° C. with stirring with a magnetic stirrer. In another two-necked eggplant-type flask, a suspension of 41.7 mg of N-bromosuccinimide (manufactured by FUJIFILM Wako Pure Chemical Corporation) in 2 mL of dichloromethane (manufactured by FUJIFILM Wako Pure Chemical Corporation, super-dehydrated) was placed, and the suspension was cooled to 0° C. The suspension was added to the dichloromethane solution of 2H-4PS using a cannula. The mixture was stirred at −40° C. for 30 minutes, and then a saturated aqueous sodium bicarbonate solution (30 mL) was added to the reaction solution, followed by washing with dichloromethane (30 mL) three times. To the washed organic layer (bottom layer), a 0.2 M aqueous solution of sodium thiosulfate (60 mL) was added, and the reaction solution was stirred for 30 minutes. The reaction solution was extracted with dichloromethane (30 mL) three times. $Na_2SO_4$ was added to the mixed organic layer, and the mixture was stirred for about 30 minutes to remove moisture. Then, solids were filtered off from the mixture, and the resulting solution was concentrated by a rotary evaporator to obtain 2Br-4PS (crude product 97.3 mg). 2Br-4PS was not further purified and used for the subsequent reaction.

Synthesis of Dimethylthiolated Hexamer (2MeS-6PS)

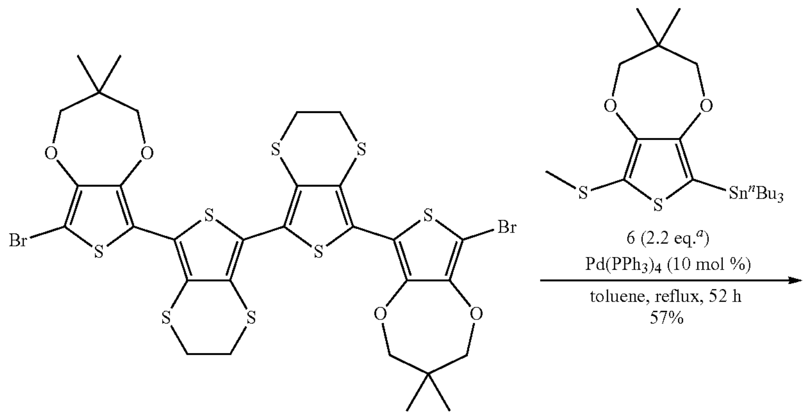

2Br-4PS

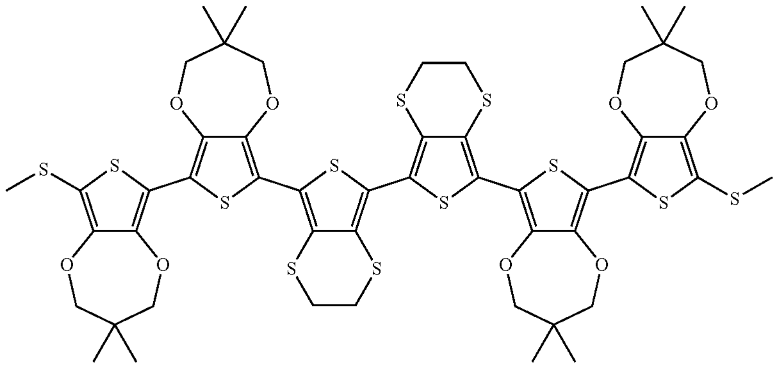

2MeS-6PS

A two-neck eggplant-type flask (reaction vessel) with a volume of 50 mL was prepared, and a stirrer was placed therein. The flask was sealed with a septum, and heated the wall surface thereof with a heat gun for about 1 minute while being evacuated with a vacuum pump to remove moisture. Then, the atmosphere inside the reaction vessel was replaced with argon. This procedure was repeated three times. The septum of the other two-necked eggplant-type flask was opened under argon flow, and 97 mg of 2Br-4PS (crude product), total amount of monomer 6 (crude product), and 13.2 mg of tetrakis(triphenylphosphine)palladium were placed in the flask, and the flask was capped with septum. 3.5 mL of toluene (manufactured by FUJIFILM Wako Pure Chemical Corporation) was added to the flask, and the reaction solution was refluxed for 17 hours. The reaction solution was cooled to room temperature, and black solids were removed by celite filtration. The obtained crude product was purified using a preparative HPLC equipped with a high-performance preparative GPC column, followed by purification by reprecipitation using dichloromethane as a good solvent and hexane as a poor solvent to obtain 74.4 mg (63.7 μmol) of 2MeS-6PS (a compound represented by the formula (8)) as a yellow powder in a yield of 57%.

Physical property values: $^{1}$H-NMR ($CDCl_6$, 300 MHz) δ 1.09 (s, 24H), 2.41 (2, 6H), 3.22 to 3.30 (m, 8H), 3.83 to 3.88 (m, 16H); $^{13}$C-NMR ($CDCl_3$, 75 MHz) δ 21.4, 21.7, 21.8, 28.4, 28.9, 39.1, 39.2, 80.2, 80.3, 80.3, 80.6, 113.2, 113.3, 115.4, 116.8, 123.9, 124.8, 127.3, 128.6, 145.0, 145.6, 146.6, 150.9.

Comparative Example 1

Synthesis of Compound

The compound represented by the following formula (C1) was synthesized in accordance with the method described in Example 1 of WO 2020/262443 A1.

(C1)

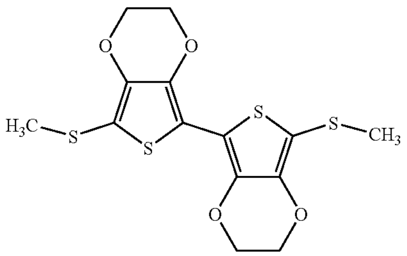

Preparation of Composition 4

In "Preparation of composition" of Example 1, 3.7 mg of the compound represented by the formula (C1) was used in place of the compound represented by the formula (4). 10 mg of $n\text{-}Bu_4NClO_4$ (manufactured by Tokyo Chemical Industry Co., Ltd.: a counter anion is $ClO_4^-$) was used as a dopant in place of $n\text{-}Bu_4NPF_6$. Except for the above, composition 4 was obtained in the same manner as in "Preparation of composition" of Example 1. Asa result of the single crystal structure analysis, the doping ratio was 50%.

Comparative Example 2

Synthesis of Compound

A compound represented by the formula (C1) was synthesized in the same manner as in Comparative Example 1.

Preparation of Composition 5

In "Preparation of composition" of Example 1, 3.7 mg of a compound represented by the formula (C1) was used in place of the compound represented by the formula (4). Except for the above, composition 5 was obtained in the same manner as in "Preparation of composition" of Example 1. As a result of the single crystal structure analysis, the doping ratio was 50%.

2. Measurement

The following items were measured for the composition (single crystal) obtained in Examples and Comparative Examples.

(1) Electrical Resistivity ρ

A gold wire having a 15 μmφ was bonded to the composition with a conductive carbon paste (XC-12, manufactured by FUJIKURA KASEI CO., LTD.), and the electrical resistivity ρ at 25° C. was measured by a four-terminal method or a two-terminal method. In order to reduce the strain on the single crystal at the time of bonding, the Au wire was crosslinked using Ag paste (DOTITE (D-500), manufactured by FUJIKURA KASEI CO., LTD.), and connected to the substrate. The carbon paste and Ag paste were mixed with a small amount of butyl glycol acetate (manufactured by Tokyo Chemical Industry Co., Ltd.), and used to make them to have moderate viscosity. The results are shown in Table 1.

(2) Activation-Energy $E_a$

The electrical resistivities ρ of the composition were measured with varying temperatures in the range of 25° C. to −263° C. and plotted on a graph (x-axis: inverse of temperature [K] converted to Kelvin temperature, y-axis: natural logarithm of electrical resistivity ρ [Ωcm]). The slope at 0° C. of the curve made by connecting the plots was employed as the activation-energy $E_a$ at 0° C. The results are shown in Table 1.

TABLE 1

| | Compound | Dopant (dopant source) | Doping ratio [%] | Oxidation method (solvent used) | Electrical resistivity ρ [Ω cm] | Activation-energy $E_a$ [meV] |
|---|---|---|---|---|---|---|
| Composition 1 | Formula (4) | $PF_6^-$ (n-$Bu_4NPF_6$) | 50% | Electrolytic oxidation (acetone) | $2.8 \times 10^{-2}$ | 50.6 ± 0.9 |
| Composition 2 | Formula (4) | $F_2TCNQ^-$ ($F_2TCNQ$) | 50% | Chemical oxidation (dichloromethane) | 7.7 | 92.7 ± 0.2 |
| Composition 3 | Formula (5) | $HSO_4^-$ (n-$Bu_4HSO_4$) | 50% | Chemical oxidation (acetone) | $2.3 \times 10^{3}$ | 170.2 ± 1.6 |
| Composition 4 (Comparative) | Formula (C1) | $ClO_4^-$ (n-$Bu_4ClO_4$) | 50% | Electrolytic oxidation (acetone) | $4.4 \times 10^{3}$ | 223.6 ± 0.5 |
| Composition 5 (Comparative) | Formula (C1) | $PF_6^-$ (n-$Bu_4NPF_6$) | 50% | Electrolytic oxidation (acetone) | $4.4 \times 10^{4}$ | 277.9 ± 1.4 |

3. Evaluation

From Table 1, it was found that the electrical resistivities ρ of the compositions 1 to 3 using the compound according to an aspect of the invention were smaller than those of the compositions 4 and 5 using the comparative compound. The compositions 1 to 3 have significantly lower activation-energy $E_a$ compared to those of the compositions 4 and 5, which is considered to contribute to a decrease in the electrical resistivity ρ.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The documents described in the specification and the specification of Japanese application(s) on the basis of which the present application claims Paris convention priority are incorporated herein by reference in its entirety.

The invention claimed is:

1. An electrode, comprising:

a compound represented by the following formula (1-3) and (1-4):

$$Z^1\text{-}\alpha_a\text{-}\beta_b\text{-}\gamma_c\text{-}Z^2 \quad (1\text{-}3)$$

$$Z^1\text{-}\alpha_a\text{-}\beta_b\text{-}\gamma_c\text{-}\delta_d\text{-}Z^2 \quad (1\text{-}4)$$

wherein in the formula (1-3) and (1-4),

α is a unit represented by the following formula (1α), and a is an integer of 1 to 10; when a is two or more, two or more units α are the same as each other;

β is a unit represented by the following formula (1β), and b is an integer of 1 to 10; when b is two or more, two or more units β are the same as each other;

γ is a unit represented by the following formula (1γ), and c is an integer of 1 to 10; when c is two or more, two or more units γ are the same as each other;

δ is a unit represented by the following formula (1δ), and d is an integer of 0 to 10; when d is two or more, two or more units δ are the same as each other;

the structure of unit α is different from the structure of unit β;

the structure of unit β is different from the structure of unit γ;

the structure of unit γ is different from the structure of unit δ;

$Z^1$ and $Z^2$ are independently $Y^1$, $Y^2R^1$, or $CR^2R^3R^4$;

$Y^1$ is F (fluorine atom), Cl (chlorine atom), Br (bromine atom), I (iodine atom), or a substituted or unsubstituted aryl group including 6 to 22 ring carbon atoms, and when two $Y^1$'s are present, the two $Y^1$'s are the same as or different from each other;

$Y^2$ is S (sulfur atoms), Se (selenium atom), O (oxygen atom), Te (tellurium atom), $SO_3$ (S is a sulfur atom, O is an oxygen atom), $SO_2$ (S is a sulfur atom, O is an oxygen atom), or $PO_3$ (P is a phosphorus atom, O is an oxygen atom), and when two $Y^2$'s are present, the two $Y^2$'s are the same as or different from each other;

$R^1$ to $R^4$ are independently H (hydrogen atom), a substituted or unsubstituted alkyl group including 1 to 12 carbon atoms, or a substituted or unsubstituted aryl group including 6 to 22 ring carbon atoms;

when two $R^1$'s are present, the two $R^1$'s are the same as or different from each other;

when two $R^2$'s are present, the two $R^2$'s are the same as or different from each other;

when two $R^3$'s are present, the two $R^3$'s are the same as or different from each other;

when two $R^4$'s are present, the two $R^4$'s are the same as or different from each other;

(1α)

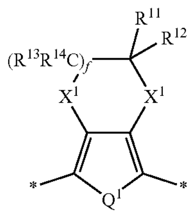

wherein in the formula (1α), $Q^1$ is S (sulfur atom), Se (selenium atom), O (oxygen atom), Te (tellurium atom), or NH;

$X^1$ is S (sulfur atom), Se (selenium atom), O (oxygen atom), or Te (tellurium atom), and two $X^1$'s are the same as each other;

$R^{11}$ to $R^{14}$ are independently H (hydrogen atom) or an unsubstituted alkyl group including 1 to 12 carbon atoms;

f is an integer of 1 to 3;

when f is two or more, two or more $R^{13}$'s are the same as or different from each other, and two or more $R^{14}$'s are the same as or different from each other;

(1β)

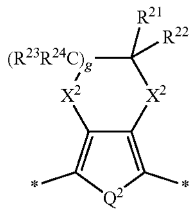

wherein in the formula (1β), $Q^2$ is S (sulfur atom), Se (selenium atom), O (oxygen atom), Te (tellurium atom), or NH;

$X^2$ is S (sulfur atom), Se (selenium atom), O (oxygen atom), or Te (tellurium atom), and two $X^2$'s are the same as each other;

$R^{21}$ to $R^{24}$ are independently H (hydrogen atom) or an unsubstituted alkyl group including 1 to 12 carbon atoms;

g is an integer of 1 to 3;

when g is two or more, two or more $R^{23}$'s are the same as or different from each other, and two or more $R^{24}$'s are the same as or different from each other;

(1γ)

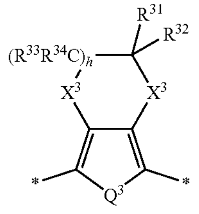

wherein in the formula (1γ), $Q^3$ is S (sulfur atom), Se (selenium atom), O (oxygen atom), Te (tellurium atom), or NH;

$X^3$ is S (sulfur atom), Se (selenium atom), O (oxygen atom), or Te (tellurium atom), and two $X^3$'s are the same as each other;

$R^{31}$ to $R^{34}$ are independently H (hydrogen atom) or an unsubstituted alkyl group including 1 to 12 carbon atoms;

h is an integer of 1 to 3;

when h is two or more, two or more $R^{33}$'s are the same as or different from each other, and two or more $R^{34}$'s are the same as or different from each other;

(1δ)

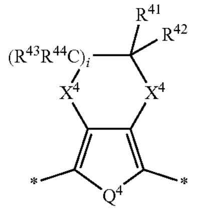

wherein in the formula (1δ), $Q^4$ is S (sulfur atom), Se (selenium atom), O (oxygen atom), Te (tellurium atom), or NH;

$X^4$ is S (sulfur atom), Se (selenium atom), O (oxygen atom), or Te (tellurium atom), and two $X^4$'s are the same as each other;

$R^{41}$ to $R^{44}$ are independently H (hydrogen atom) or an unsubstituted alkyl group including 1 to 12 carbon atoms, i is an integer of 1 to 3;

when i is two or more, two or more $R^{43}$'s are the same as or different from each other, and two or more $R^{44}$'s are the same as or different from each other.

2. The electrode of claim 1, wherein two or more selected from the group consisting of a, b, c, and d, are the same integer.

3. The electrode of claim 1, wherein one or more selected from the group consisting of a, b, c, and d, are an integer of 1 to 6.

4. The electrode of claim 1, wherein one or more selected from the group consisting of a, b, c, and d, are an integer of 1 to 4.

5. The electrode of claim 1, wherein one or more selected from the group consisting of f, g, h, and i, are 1 or 2.

6. The electrode of claim 1, wherein one or more selected from the group consisting of f, g, h, and i, are 1.

7. The electrode of claim 1, wherein one or more units selected from the group consisting of the unit α, the unit β, the unit γ, and the unit δ, are represented by the following formula (2), and when two or more units selected from the group consisting of the unit α, the unit β, the unit γ, and the unit δ, are represented by the following formula (2), the structures of the two or more units are the same as or different from each other:

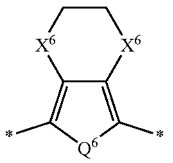
(2)

wherein in the formula (2), $Q^6$ is S (sulfur atom), Se (selenium atom), O (oxygen atom), Te (tellurium atom), or NH; and $X^6$ is S (sulfur atom), Se (selenium atom), O (oxygen atom), or Te (tellurium atom), and two $X^6$'s are the same as each other.

8. The electrode of claim 7, wherein $Q^6$ is S (sulfur atom).

9. The electrode of claim 7, wherein $X^6$ is S (sulfur atom) or O (oxygen atom).

10. The electrode of claim 1, wherein one or more units selected from the group consisting of the unit α, the unit β, the unit γ, and the unit δ, are represented by the following formula (3), and when two or more units selected from the group consisting of the unit α, the unit β, the unit γ, and the unit δ, are represented by the following formula (3), the structures of the two or more units are the same as or different from each other:

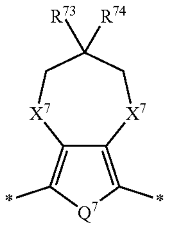
(3)

wherein in the formula (3), $Q^7$ is S (sulfur atom), Se (selenium atom), O (oxygen atom), Te (tellurium atom), or NH;

$X^7$ is S (sulfur atom), Se (selenium atom), O (oxygen atom), or Te (tellurium atom), and two $X^7$'s are the same as each other;

$R^{73}$ and $R^{74}$ are independently H (hydrogen atom) or an unsubstituted alkyl group including 1 to 12 carbon atoms.

11. The electrode of claim 10, wherein $Q^7$ is S (sulfur atom).

12. The electrode of claim 10, wherein $X^7$ is S (sulfur atom) or O (oxygen atom).

13. The electrode of claim 10, wherein $R^{73}$ and $R^{74}$ are independently an alkyl group including 1 to 12 carbon atoms.

14. The electrode of claim 1, wherein $Z^1$ and $Z^2$ are independently an alkylthio group including 1 to 12 carbon atoms or an alkylseleno group including 1 to 12 carbon atoms.

15. The electrode of claim 1, wherein d=0.

16. The electrode of claim 15, wherein the structure of the unit α and the structure of the unit γ are the same as each other.

17. The electrode of claim 15, wherein a=c.

18. The electrode of claim 1, wherein d is 1 or more.

19. The electrode of claim 1, further comprising:

a dopant.

20. The electrode of claim 19, wherein the dopant is one or more selected from the group consisting of $BF_4^-$, $ClO_4^-$, $PF_6^-$, $HSO_4^-$, $GaCl_4^-$, $CoCl_4^{2-}$, $SbF_6^-$, $SCN^-$, $Cl^-$, $Br^-$, $I^-$, $Br_3^-$, $I_3^-$, and a monovalent anionic species of TCNQ or $F_x$TCNQ where x is 2 or 4.

21. The electrode of claim 1, wherein the electrical resistivity ρ at 25° C. is $10^5$ Ωcm or lower.

22. The electrode of claim 1, wherein the activation-energy $E_a$ at 0° C. is 300 meV or lower.

23. The electrode of claim 1, wherein the structures of two or more α, β, γ, and δ are the same as each other.

24. The electrode of claim 1, wherein the which is configured for a condenser, a battery, or a capacitor, or is a transparent electrode.

* * * * *